(12) United States Patent
Burns et al.

(10) Patent No.: US 7,750,094 B2
(45) Date of Patent: Jul. 6, 2010

(54) ADDUCTS AND CURABLE COMPOSITIONS USING SAME

(75) Inventors: Barry N. Burns, Killiney (IE); Ray P. Tully, Slane (IE); Jonathan P. Wigham, Rathfarnham (IE); Martin J. Fitzpatrick, Harolds Cross (IE); Rainer Schoenfeld, Duesseldorf (DE); Ciaran B. McArdle, Dublin (IE); Mark Loane, Blanchardstown (IE)

(73) Assignees: Loctite (R&D) Limited, Dublin (IE); Henkel AG & Co., KGaA, Duesseldorf (DE)

(*) Notice: Subject to any disclaimer, the term of this patent is extended or adjusted under 35 U.S.C. 154(b) by 0 days.

(21) Appl. No.: 12/410,009

(22) Filed: Mar. 24, 2009

(65) Prior Publication Data

US 2009/0234079 A1 Sep. 17, 2009

Related U.S. Application Data

(63) Continuation of application No. PCT/IE2007/000087, filed on Sep. 25, 2007.

(51) Int. Cl.
*C08L 83/12* (2006.01)
(52) U.S. Cl. ............... 525/476; 528/27; 528/28
(58) Field of Classification Search .......... None
See application file for complete search history.

(56) References Cited

U.S. PATENT DOCUMENTS

| | | | |
|---|---|---|---|
| 3,179,622 A | | 4/1965 | Haluska |
| 3,332,900 A | | 7/1967 | Reischl et al. |
| 3,332,975 A | | 7/1967 | John et al. |
| 3,830,785 A | | 8/1974 | Matsui et al. |
| 4,607,091 A | | 8/1986 | Schreiber |
| 5,021,484 A | | 6/1991 | Schreiber et al. |
| 5,084,532 A | | 1/1992 | Schenkel |
| 5,200,452 A | | 4/1993 | Schreiber |
| 5,278,257 A | | 1/1994 | Muelhaupt et al. |
| 5,443,911 A | | 8/1995 | Schreiber et al. |
| 5,543,516 A | | 8/1996 | Ishida |
| 6,160,148 A | * | 12/2000 | Dauth et al. ............ 556/419 |
| 6,281,321 B1 | * | 8/2001 | Kelly et al. ............. 528/17 |
| 6,566,322 B1 | | 5/2003 | Brook et al. |
| 2004/0137155 A1 | | 7/2004 | Bernheim |
| 2005/0074618 A1 | | 4/2005 | King et al. |

FOREIGN PATENT DOCUMENTS

| | | | |
|---|---|---|---|
| DE | 4011942 | | 10/1990 |
| DE | 198 17 776 A1 | * | 10/1999 |
| DE | 10003322 | | 8/2001 |
| GB | 1128642 | | 9/1968 |
| JP | 8-92404 A | * | 4/1996 |
| WO | WO 03/044264 | | 5/2003 |
| WO | WO2005/007766 A1 | | 1/2005 |

OTHER PUBLICATIONS

S. Maier, et al. "Carbonylbiscaprolactam: A Versatile Reagent for Organic Synthesis and isocyana Free Urethane Chemistry", *Angew. Chem. Int.* Ed., vol. 42, pp. 5094-5097 (2003).
W.J. Burke et al., "A new Aminoalkylation Reaction. Condensation of Phenols with Dihydro-1 aroxazines", *Journal Organic Chemistry*, vol. 30 (10), p. 3423-3427 (1965).
ASTM D1876—"Standard Test Method for Peel Resistance of Adhesives".
ASTM D1002—"Standard Test Method for Apparent Shear Strength of Single-Lap-Joint Adhesiv Bonded Metal Specimens by Tension Loading".
International Search Report dated Oct. 22, 2008.
Bumgardner C.L. et al., "O-Phenylhydroxylamine" *Chem. Ind.*, pp. 559-560, XP009094581, p. 560, left-hand col., lines 22,23 (Mar. 24, 1962).
Steffen Maier et al., "Isocyanate-Free Route To Caprolactam-Blocked Oligomeric Isocyanates Carbonylbiscaprolactam-(CBC) Mediated End Group Conversion" Macromolecules, ACS, Washington, D.C., U.S., vol. 36, pp. 4727-4734, EX002476633, (2003).
Buchholz U. et al., "Branched Polysiloxane Block Copolymers as Expoxy Toughening Agents", *ACS Polym. Prepr.*, 22, 1, pp. 205-206 (1992).
"Toughened Epoxy Composition for Laminate Fabrication", IBM Technical Disclosure Bulletin, 24, p. 964 (1981).
Anand Prabu A. et al., "Mechanical and Electrical Studies of Silicone Modified Polyurethane-Epoxy Intercrosslinked Networks", *Polymer Journal*, 36, 10, pp. 848-855 (2004).
Ekin et al., "Synthesis and Characterization of Novel Hydroxyalkyl Carbamate and Dihydroxyalkyl Carbamate Terminated Poly(dimethylsiloxane) Oligomers and Their Block Copolymers with Poly(.epsilon.-caprolactone)", Macromolecules, 39(25), 8659-8668 (2006).

* cited by examiner

*Primary Examiner*—Marc S Zimmer
(74) *Attorney, Agent, or Firm*—Steven C. Bauman

(57) ABSTRACT

The present invention relates to novel adducts useful for improving the toughness and curable compositions using such toughening adducts. In a particular aspect, the present invention relates to novel toughening adducts and curable compositions having improved fracture toughness using those toughening adducts.

17 Claims, No Drawings

ADDUCTS AND CURABLE COMPOSITIONS USING SAME

BACKGROUND OF THE INVENTION

1. Field of the Invention

The present invention relates to novel adducts useful for improving toughness, and curable compositions using such adducts. The novel adducts may improve toughness, such as in terms of impact resistance, and/or adhesion in curable compositions using those adducts.

2. Brief Description of Related Technology

Toughness generally is the ability of a material to absorb energy and undergo large permanent set without rupture. For many engineering adhesive applications, toughness is often the deciding factor. Plastics, because of their inherent brittleness, have heretofore been modified in a variety of ways in efforts to improve the toughness thereof. Epoxy resins, for example, which form a versatile glassy network when cured, exhibit excellent resistance to corrosion and solvents, good adhesion, reasonably high glass transition temperatures ($T_g$) and adequate electrical properties. Unfortunately, however, the poor fracture toughness of epoxy resins oftentimes limits the usefulness thereof in many commercial applications.

The impact strength, as well as other physical properties of crosslinked epoxy resins, is controlled by the chemical structure and molecular weight of the epoxy resin, weight ratio of the epoxy resin to the hardener, by any added fillers, and by the conditions used to cure the formulation. Unfortunately, crosslinked, glassy epoxy resins with a relatively high glass transition temperature ("$T_g$") (>100° C.) are brittle in nature. The poor impact strength of high glass transition epoxy resins limits their usage as structural materials and use in or as composites.

Conventional toughening agents (e.g., carboxyl terminated butadiene nitrile rubbers, "CTBN") are frequently unsuitable as additives in formulations where low temperature crash impact performance is desired.

Carbonyl biscaprolactam, such as is available commercially under the ALLINCO brand name from DSM Research, has been reported as a versatile, nontoxic reagent that converts hydroxy and amino groups of functional polymers into the corresponding caprolactam-blocked isocyanates without requiring the use of isocyanates. See Angew. Chem. Int. Ed., 42, 5094-5097 (2003). For instance, in the context of primary amines, see the following reaction scheme I:

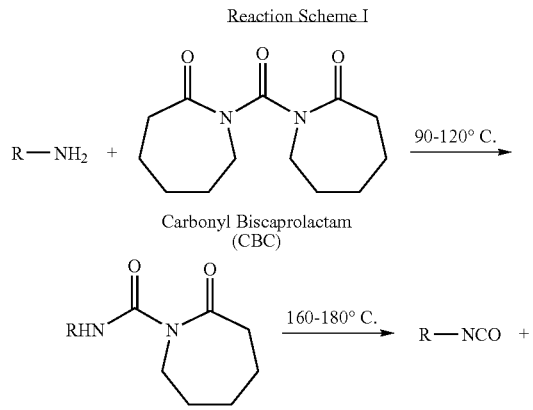

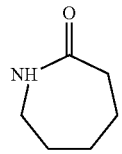

In addition, U.S. Pat. No. 5,278,257 (Mulhaupt) and International Patent Publication No. WO 2005/007766 A1 describe the preparation of a rubber modified epoxy composition containing a phenol-capped polyurethane pre-polymer as a toughening agent. The so-described toughening agents are believed to be the basis of the BETAMATE-brand product offering from Dow Automotive.

The low temperature performance properties of such BETAMATE-brand products could stand improvement. In addition, consumers would benefit from the offering of additional adducts and products using such adducts having different or more desirable physical property performance.

Accordingly, there is a need for novel adducts that are effective for improving the toughness of adhesive formulations, especially in formulations requiring good low temperature performance, and which formulations are based on thermosets such as epoxy, episulfides and/or benzoxazines.

SUMMARY OF THE INVENTION

In accordance with the present invention, there are provided novel adducts which are useful for improving the performance properties of thermosetting resin formulations, such as those based on epoxy, episulfide, benzoxazine and combinations thereof. The performance properties include improved impact resistance and adhesion to substrate surfaces.

The novel adducts may be represented by compounds within general formula I.

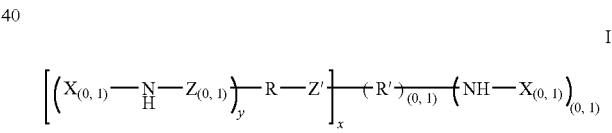

where R and R' are each independently selected from polyethers, such as polypropylenel glycol ("PPG") and polyTHF, perfluorinated polyethers ("PFP"), JEFFAMINE type backbones (as more fully described below), polydimethylsiloxane ("PDMS") backbones (again, as more fully described below), LP3 type backbones (as more fully described below), and hydroxy terminated polybutadiene ("HPBD") backbones, provided however that when R is PPG, R'is not PPG or X is not ArO;

Z and Z' are each independently selected from —$CH_2$—K—$(NH)_{(0,1)}$CO—, where K is $C_1$-$C_{70}$ linear or branched alkylene or alyleneoxy, $C_5$-$C_{12}$ cycloalkylene or cycloalkyleneoxy, or $C_6$-$C_{15}$ arylene or aryleneoxy;

X is selected from ArO—, ArO—C=O, or mercapto- or amino-functionalized alkylene or alkylenoxy urea, urethane or thiourethane, where Ar is for example phenyl, biphenyl, bisphenol A, bisphenol F, bisphenol S, bisphenol E, allyl, alkyl, alkenyl, carboxy, N-carbamoyl functionalized five to seven membered cyclic amides, epoxy ether or hydroxyl-functionalized ether; and y is 1-4, and x is 1-3.

The novel adducts may be represented by compounds within general formula II.

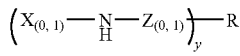

II where X, Z, R and y are as defined above.

For epoxy functionalized adducts, they may be represented by compounds within general formula III.

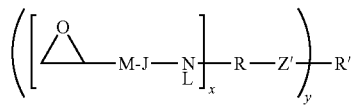

III where M is an alkylene, cycloalkylene, or arylene linkage;

J is a linkage such as hydroxyalkylene (such as hydroxy ethylene), —OC=O, or a ring structure with L such as,

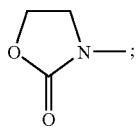

L is H or a ring structure with J as described above; and R, Z', R', x and y are as defined above.

For phenol-functionalized adducts, they may be represented by compounds within general formula IV.

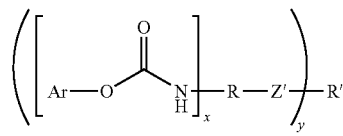

IV where Ar is an aryl group, and R, Z', R', x and y are as defined above.

For N-carbamoyl functionalized five to seven membered cyclic amide adducts, they may be represented by compounds within general formula V.

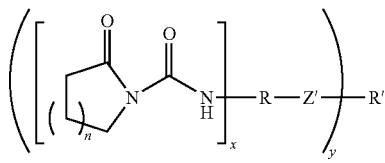

V where R, Z', R', n, x and y are as defined above.

In order to improve low temperature fracture toughness performance properties, while conferring improved adhesion on substrates, such as steel, the inventive adducts should also have a low Tg value, such as below room temperature, desirably −20° C. and more desirably −40° C. or lower. In addition, other physical properties of the adduct may contribute to such low temperature performance, such as compatibility with the thermoset matrix and solubility parameters generally. To that end, the level of PDMS in R of the adduct, for instance, may be adjusted if desired within the range of about 5 to about 95%, such as about 20 to about 80%, desirably about 20% by weight of R in the adduct, to provide the adduct with the desirable Tg, particularly for improving wedge impact performance and improved adhesion. To the extent that R in the adduct is composed of a second (or third) backbone, the remaining portion of R may be a non-silicon-containing segment, such as one derived from a polypropylene glycol, of course bearing (meth)acrylate functionalization.

Adducts within formula I have been found to be useful as additives in one part thermosetting resin compositions, so as to improve physical properties, such as tensile peel strength values, tensile shear strength values and wedge impact properties.

DETAILED DESCRIPTION OF THE INVENTION

As noted above, the present invention provides novel adducts which are useful for improving the performance properties of thermosetting resin formulations, such as those based on epoxy, episulfide, benzoxazine and combinations thereof.

The novel adducts may be represented by compounds within general formula I.

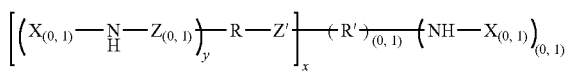

I where R and R' are each independently selected from polyethers, such as PPG and polyTHF, PFP, JEFFAMINE type backbones, PDMS backbones, LP3 type backbones, and HPBD backbones, provided however that when R is PPG, R' is not PPG or X is not ArO;

Z and Z' are each independently selected from —CH$_2$— K—(NH)$_{(0,1)}$CO—, where K is C$_1$-C$_{70}$ linear or branched alkylene or alyleneoxy, C$_5$-C$_{12}$ cycloalkylene or cycloalkyleneoxy, or C$_6$-C$_{15}$ arylene or aryleneoxy;

X is selected from ArO—, ArO—C=O, or mercapto- or amino-functionalized alkylene or alkylenoxy urea, urethane or thiourethane, where Ar is for example phenyl, biphenyl, bisphenol A, bisphenol F, bisphenol S, bisphenol E, allyl, alkyl, alkenyl, carboxy, N-carbamoyl functionalized five to seven membered cyclic amides, epoxy ether or hydroxyl-functionalized ether; and y is 1-4, and x is 1-3.

The novel adducts may be represented by compounds within general formula II.

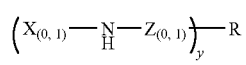

II where X, Z, R and y are as defined above.

For epoxy functionalized adducts, they may be represented by compounds within general formula III.

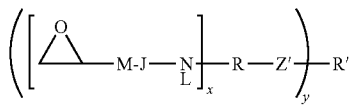

where M is an alkylene, cycloalkylene, or arylene linkage;

J is a linkage such as hydroxyalkylene (such as hydroxy ethylene), —OC=O, or a ring structure with L such as,

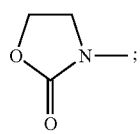

L is H or a ring structure with J as described above; and R, Z', R', x and y are as defined above.

For phenol-functionalized adducts, they may be represented by compounds within general formula IV.

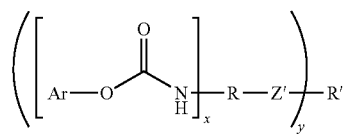

where Ar is an aryl group, and R, Z', R', x and y are as defined above.

For N-carbamoyl functionalized five to seven membered cyclic amide adducts, they may be represented by compounds within general formula V.

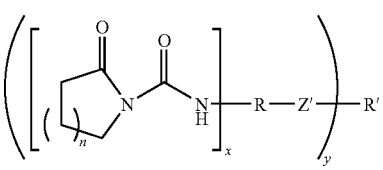

where n is 0-2 and R, Z', R', x and y are as defined above.

With reference to the building blocks used to prepare the inventive adducts, the linkage represented by "R" and "R'" may be formed from polyethers and polythioethers functionalized with one or more of hydroxy, mercapto and amino groups. Such polyethers may originate from commercially available starting materials, for instance the amine-functionalized polyethers sold under the JEFFAMINE tradename, the mercapto-functionalized polythioethers sold under the LP-3 tradename and/or the hydroxy-functionalized polyethers sold under the trade designation, PPG.

Each of these different functionalized polyethers and polythioethers are available commercially, or can be prepared, in a variety of molecular weights. With the different molecular weights, physical property changes can be imported into the inventive adduct to tailor the adduct for the specific end use application for which it is intended to be used.

Amine-functionalized polyethers include oxyethylene diamines, oxyethylene triamines, polyoxyethylene diamines, polyoxyethylene triamines, oxypropylene diamines, oxypropylene triamines, polyoxypropylene diamines, polyoxypropylene triamines, dimethylene glycol dipropyl amine and/or derivatives and adducts thereof, and combinations thereof.

Commercially available examples of such polyether amine-based hardeners—amine-functionalized polyethers—include those from BASF Corporation, Mt. Olive, N.J., under the trade designation 4, 7, 10 TTD, and Huntsman Corporation, Houston, Tex., under the JEFFAMINE tradename, such as JEFFAMINE D-230, JEFFAMINE D-400, JEFFAMINE D-2000, JEFFAMINE T-403, JEFFAMINE ED-600, JEFFAMINE ED-900, JEFFAMINE ED-2001, JEFFAMINE EDR-148, JEFFAMINE XTJ-509, JEFFAMINE T-3000, JEFFAMINE T-5000, and combinations thereof.

The JEFFAMINE D series are diamine based products and may be represented by

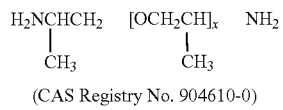

(CAS Registry No. 904610-0)

where x is about 2.6 (for JEFFAMINE D-230), 5.6 (for JEFFAMINE D-400) and 33.1 (for JEFFAMINE D-2000), respectively.

The JEFFAMINE T series are trifunctional amine products based on propylene oxide and may be represented by

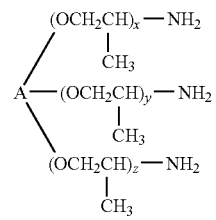

where x, y and z are set forth below in Table A.

TABLE A

| JEFFAMINE | Initiator (A) | Approx. Mol. Wt | Mole PO |
| --- | --- | --- | --- |
| T-403 | Trimethylolpropane | 440 | 5-6 |
| T-3000 | Glycerine | 3,000 | 50 |
| T-5000 | Glycerine | 5,000 | 85 |

More specifically, the JEFFAMINE T-403 product is a trifunctional amine and may be represented by

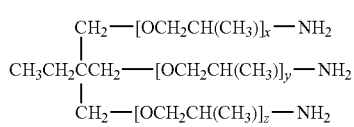

where x+y+z is 5.3 (CAS Registry No. 39423-51-3).

The JEFFAMINE ED series are polyether diamine-based products and may be represented by

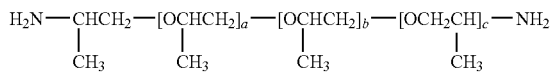

where a, b and c are set forth below in Table B.

TABLE B

| JEFFAMINE | Approx. Value | | Approx. Mol. Wt |
|---|---|---|---|
| | b | a + c | |
| ED-600 | 8.5 | 2.5 | 600 |
| ED-900 | 15.5 | 2.5 | 900 |
| ED-2001 | 40.5 | 2.5 | 2,000 |

As the mercapto-functionalized polythioethers, many materials may be used. For instance, polysulfides of the general formulae may be used

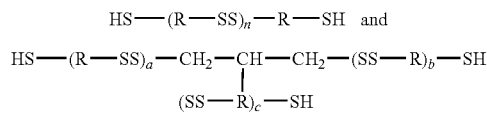

where R is an alkyl ether, such as —(CH$_2$)$_2$—O—CH$_2$—O—(CH$_2$)$_2$—, and a+b+c=n.

A particularly desirable material is known as THIOKOL LP-3, available commercially from Rohm and Haas Company, Philadelphia, Pa., where n is 6 and about 2 mole percent branching exists. LP-3 is also reported to have a molecular weight of about 1,000.

Another particularly desirable material is available commercially from Akcros Chemicals, Manchester, Great Britain under the tradename THIOPLAST, such as G1 (n is 19-21, 1.8-2 percent thiol content, and a 3,300-3,700 molecular weight), G4 (n is less than 7, less than 5.9 percent thiol content, and less than 1,100 molecular weight), G12 (n is 23-26, 1.5-1.7 percent thiol content, and a 3,900-4,400 molecular weight), G21 (n is 12-15, 2.5-3.1 percent thiol content, and a 2,100-2,600 molecular weight), G22 (n is 14-18, 2.1-2.7 percent thiol content, and a 2,400-3,100 molecular weight), G112 (n is 23-25, 1.5-1.7 percent thiol content, and a 3,900-4,300 molecular weight), and G131 (n is 30-38, 1.5-1.7 percent thiol content, and a 5,000-6,500 molecular weight). The THIOPLAST materials are reported to be prepared from the polycondensation of bis-(2-chloroethyl) formal with alkali polysulfide.

(Meth)acrylate-functionalized polydimethyl siloxanes of various molecular weights may be used as the building block for this portion of the adduct, as well.

Commercial sources for such (meth)acrylate-functionalized polydimethyl siloxanes include Genesee Silicone, Gelest Silicone and Wacker Silicones. For instance, methacryloxypropyl terminated PDMS [molecular weight 900-1200] is available from Gelest under the trade designation DMS-R11, methacryloxymethyl terminated PDMS [molecular weight ~1360] is available from Wacker under the trade designation SLM 446016-15 VP, 3-acryloxy-2-hydroxypropyl terminated PDMS [molecular weight 1000-1250] is available from Gelest under the trade designation DMS-U22, acryloxy terminated ethylene oxide PDMS [molecular weight 1500-1600] is available from Gelest under the trade designation DBE-U12 and from Goldschmidt under the trade designation TEGO V-Si 2250 [molecular weight ~2500].

Again, the different molecular weights of this segment impact desirable physical properties of the adduct, so that the resulting adduct may be more or less suitable for a variety of end use applications.

A polyalkylene glycol, such as polypropylene glycol [available commercial from Aldrich Chemical Co., molecular weight ~10,000] may also be used as a building block of the inventive adduct. Here, too, different molecular weights of this segment impact desirable physical properties of the adduct, so that the resulting adduct may be more or less suitable for a variety of end use applications.

These materials may be used as building blocks individually or they may be used in various combinations. The intended end use application will suggest to those of ordinary skill in the art whether to choose one or the other or a combination to provide the physical property set beneficial to that end use application.

Thus, for instance in order to prepare the inventive adduct with polyurethane segments, a polyol, such as trimethylol propane, would be reacted under mildly elevated temperature conditions with an isocyanate, desirably a polyisocyanate, such as hexamethylene diisocyanate, in the presence of the building block(s) of the R and R' segments.

Isocyanates suitable for use in this adduct building reaction include polyisocyanates, such as a diisocyanate (for instance an aliphatic, cycloaliphatic, aromatic or araliphatic one) or triisocyanate, or, if desirable, in combination with chain lengtheners (short-chain polyhydroxyl, polysulfhydryl or polyamine compounds), or a polyisocyanate prepolymer derived from a prepolymer polyamine, such as a prepolymer polyetheramine.

A variety of diisocyanates are useful for reaction in this regard and the choice of any particular one will be left to those persons of ordinary skill in the art, likely to be dictated in part by the commercial availability and in part by the end use properties desired.

Useful diisocyanates include ethylene diisocyanate, trimethylene diisocyanate, tetramethylene diisocyanate, pentamethylene diisocyanate, hexamethylene diisocyanate, heptamethylene diisocyanate, octamethylene diisocyanate, decamethylene diisocyanate, dodecamethylene diisocyanate, tetradecamethylene diisocyanate, hexadecamethylene diisocyanate, octadecamethylene diisocyanate, eicosamethylene diisocyanate, cyclohexamethylene diisocyanate, cyclopenthalene diisocyanate, or cyclohepthalene diisocyanate, or bis-cyclohexylene, cyclohexylmethylene diisocyanate, tetramethylxylylene diisocyanate, phenyl diisocyanate, toluene diisocyanate (such as 2,4-diisocyanatotoluene and 2,6-diisocyanatotoluene), 4,4'-diphenyl diisocyanate, 4,4'-diphenylene methane diisocyanate, dianisidine diisocyanate, 1,5-naphthalene diisocyanate, 4,4'-diphenyl ether diisocyanate, p-phenylene diisocyanate, 4,4'-dicyclo-hexylmethane diisocyanate, 1,3-bis-(isocyanatomethyl)cyclohexane, cyclohexylene diisocyanate, tetrachlorophenylene diisocyanate, 2,6-diethyl-p-phenylenediisocyanate, 3,5-diethyl-4,4'-diisocyanatodiphenyl-methane, tetramethylene diisocyanate, hexamethylene diisocyanate, ethylene diisocyanate, cyclohexylene diisocyanate, nonamethylene diisocyanate, octadecamethylene diisocyanate, 2-chloropropane diisocyanate, 2,2'-diethylether diisocyanate, 3-(dimethylamine) pentane diisocyanate, tetrachlorophenylene diisocyanate-1,4,3-heptane diisocyanate and transvinylene diisocyanate.

Additional examples of suitable isocyanates are urethanized 4,41-diisocyanatodiphenylmethane, carbodiimidized 4,4'-diisocyanatodiphenylmethane, the adduct formed from diisocyanatotoluene and trimethylolpropane, the trimer formed from diisocyanatotoluene, diisocyanato-m-xylylene, N,N'-di-(4-methyl-3-isocyanatophenyl)-urea, mixed trimerization products of diisocyanatotoluene and 1,6-diisocyanatohexamethylene, 1,6-diisocyanatohexane, 3,5,5-trimethyl-1-isocyano-3-isocyanatomethylcyclohexane (isophorene diisocyanate), N,N',N'''-tri-(6-isocyanatohexyl)-biuret, 2,2,4-trimethyl-1,6-diisocyanatohexane, 1-methyl-2,4-diisocyanatocyclohexane, diisocyanate, 4,4'-diisocyanatodicyclohexylmethane, trimeric isophorene, diisocyanate, trimeric hexane diisocyanate and methyl 2,6-diisocyanatohexanoate.

As noted above, chain lengtheners may be used as well, examples of which include diols and polyols, such as 1,4-butanediol, 1,1,1-trimethylolpropane or hydroquinone 2-hydroxyethyl ether, or diamines, such as diaminoethane, 1,6-diaminohexane, piperazine, 2,5-dimethylpiperazine, 1-amino-3-aminomethyl-3,5,5-trimethylcyclohexane, 4,4'-diaminocyclohexylmethane, 1,4-diaminocyclohexane and 1,2-propylenediamine, or hydrazine, amino acid hydrazides, hydrazides of semicarbazidocarboxylic acids, bis-hydrazides and bis-semicarbazides.

A phenolic compound may then be reacted with the isocyanate-functionalized prepolymer formed in the previous reaction step.

Phenolic compounds suitable for use in this adduct building reaction include any di- or poly-phenolic compound, though it is desirable for the phenolic compound to be a bisphenol compound, such as A, F, S or E, or a biphenol.

In general formula I, where terminal amine and/or hydroxy groups are present, they may be reacted with carbonyl biscaprolactam ("CBC") to produce the corresponding CBC-capped adducts. (See e.g. general formula V.)

Such CBC-capped adducts may be used directly as tougheners themselves in thermosetting resin formulations or they may be further reacted with other functionalized polymers (such as those polymers bearing one or more amine, hydroxyl, mercapto, epoxy or episulfide groups) to form chain extended block copolymers via a urethane or urea or thiourethane or oxazolidone linkage. These so-formed chain extended block copolymers can thus also be used to toughen thermosetting resin formulations. In addition, the use of such chain extended block copolymers can assist in compatabilizing otherwise incompatible adducts for use in thermosetting resin formulations.

The inventive adducts can be readily prepared in a variety of ways, which are discussed in the Examples section below.

Specific generalized structures of adducts within the scope of the invention include:

A

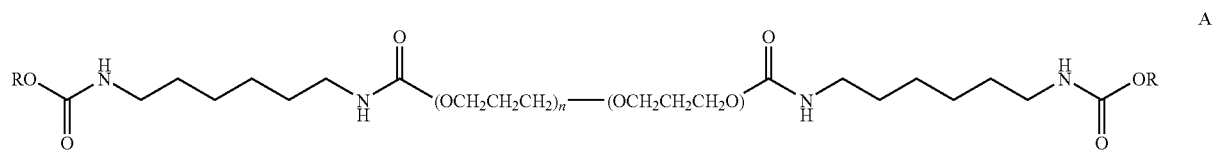

B

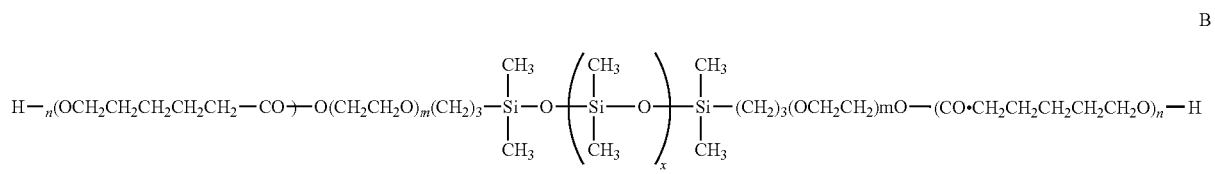

C

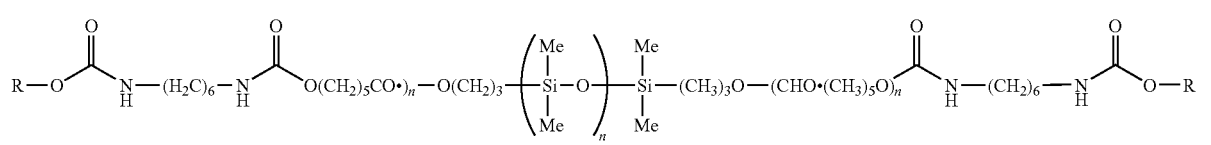

D

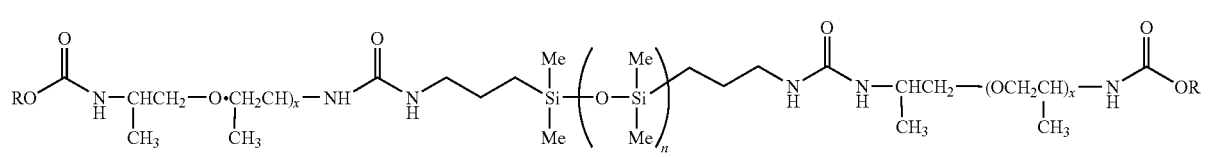

E

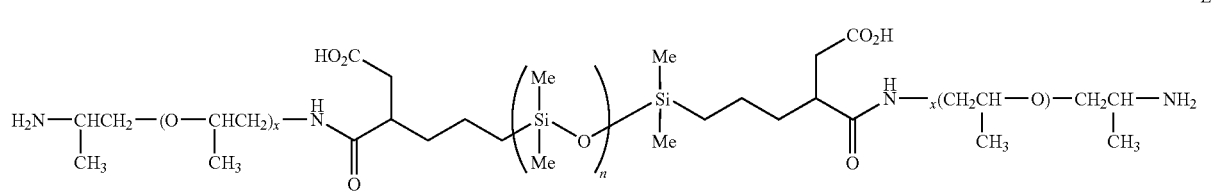

-continued
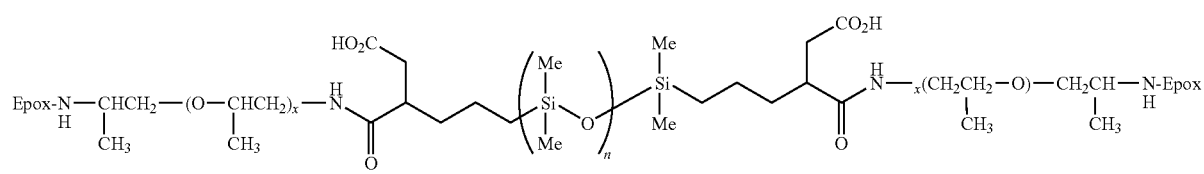
F
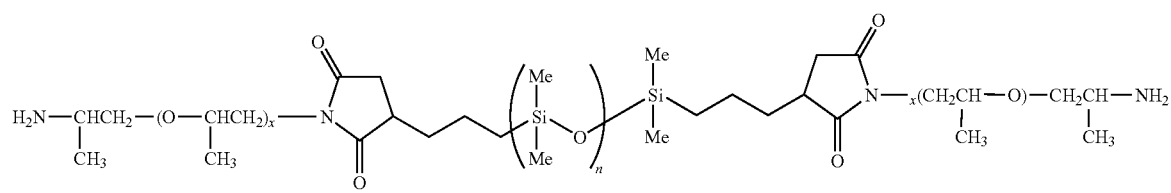
G
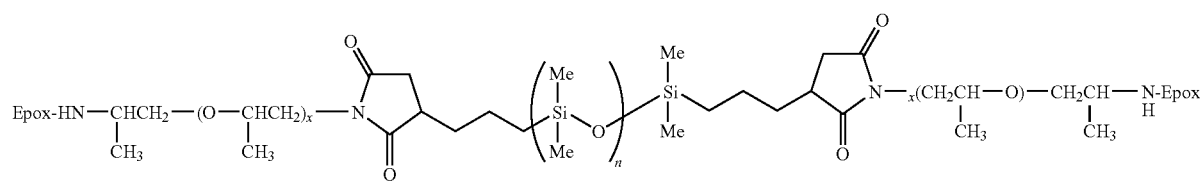
H
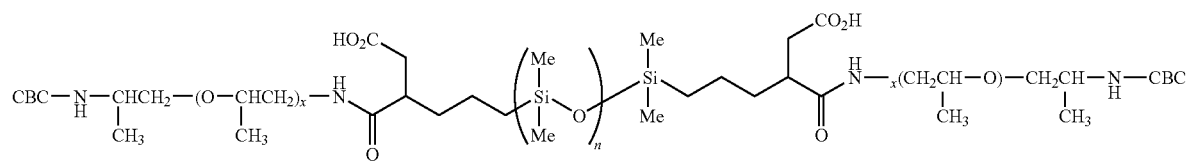
I
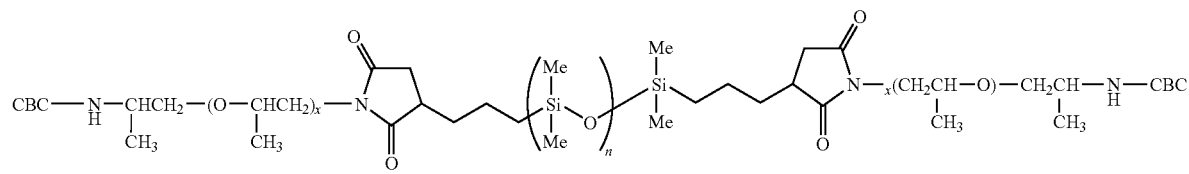
J
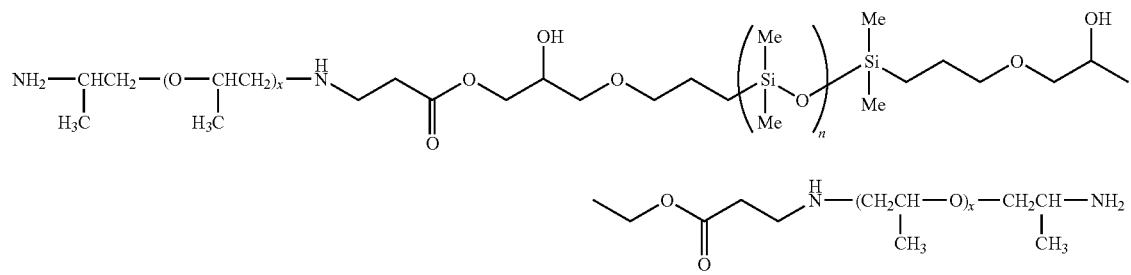
K
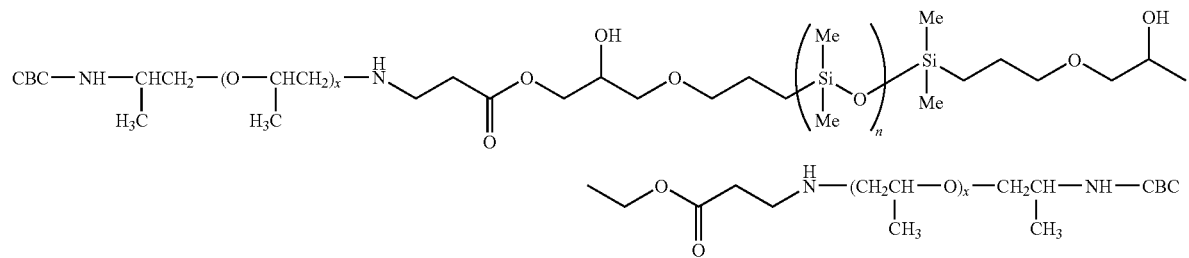
L

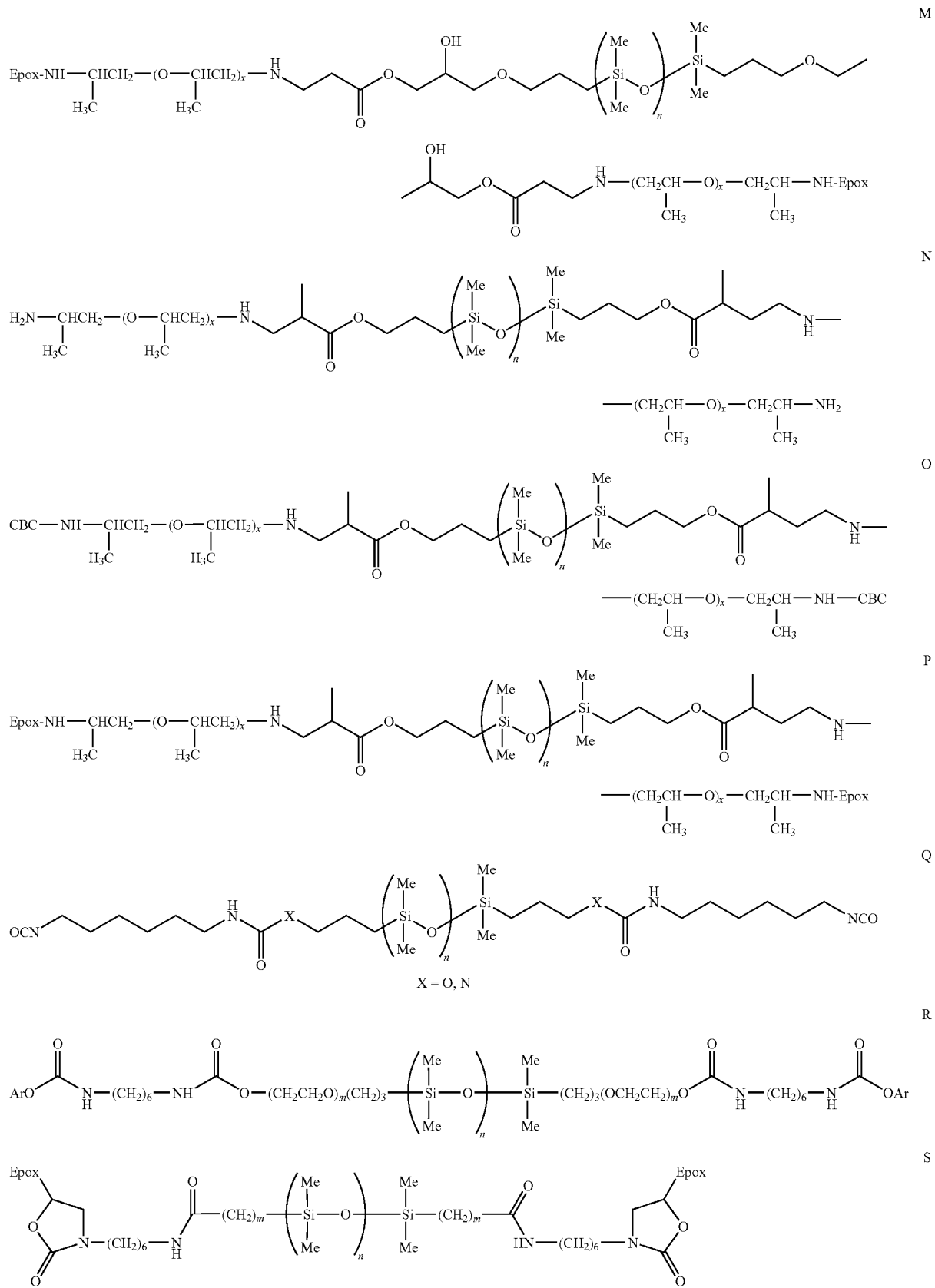

-continued
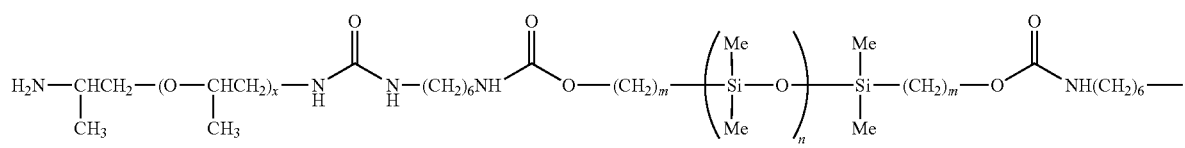
T
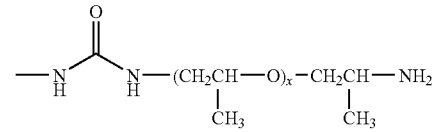
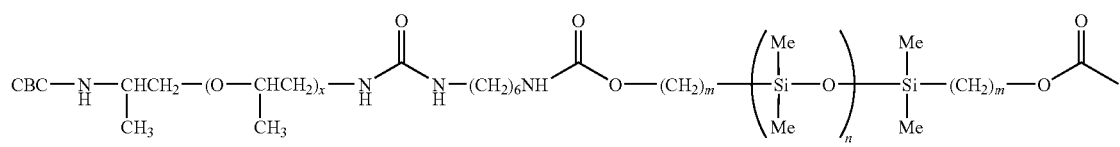
U-1
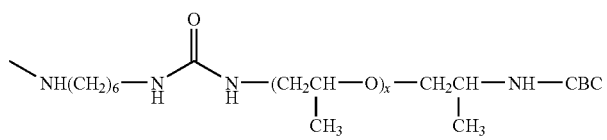
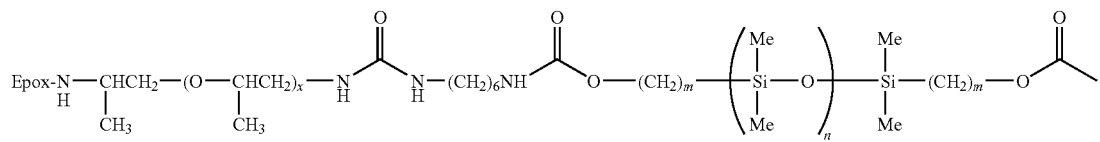
U-2
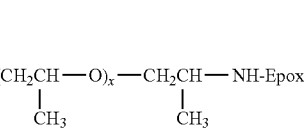
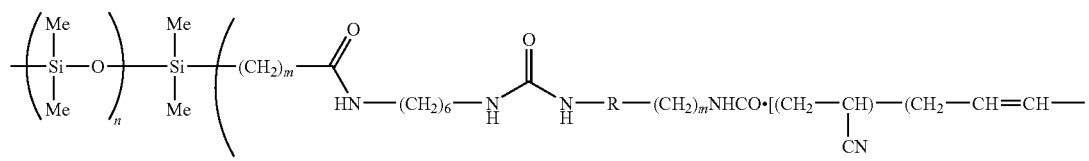
V
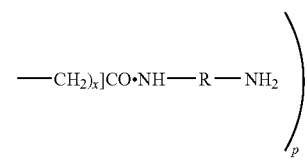
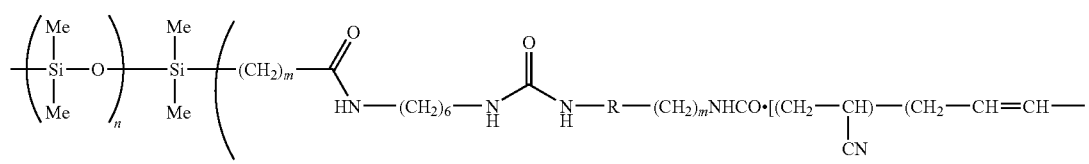
W
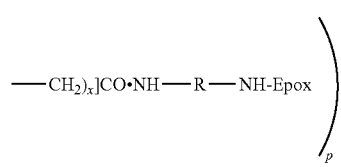

-continued

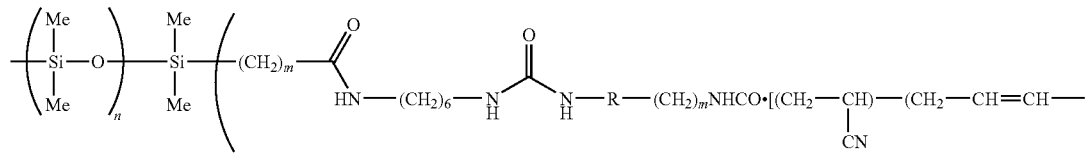 X

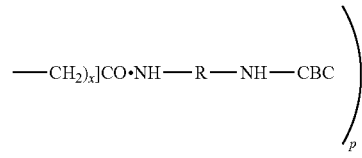

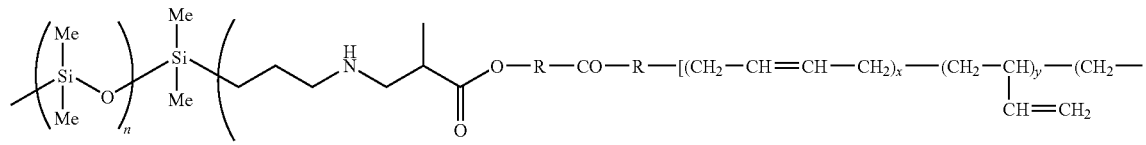 Y

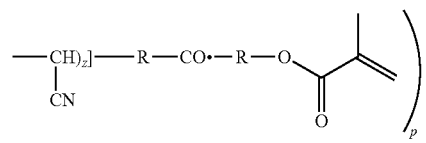

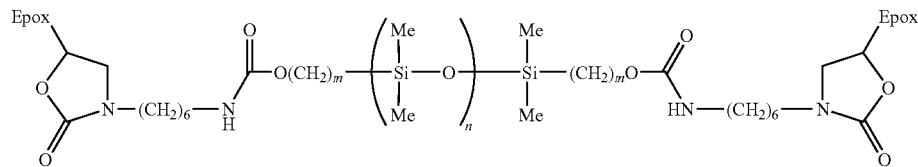 Z

R—Si(O-polyTHF-block-polyCPL)x(O-PDMS)y    AA

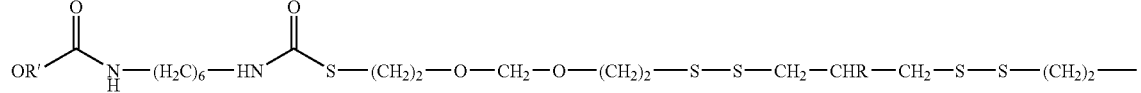 AB

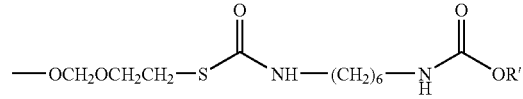

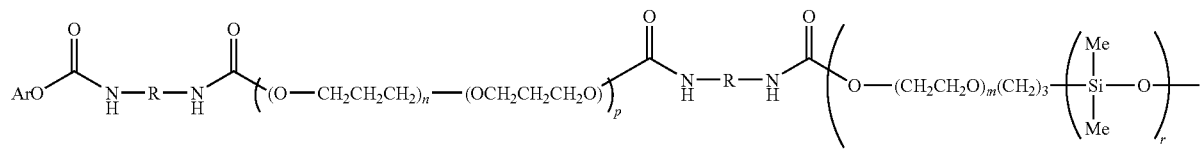 AC

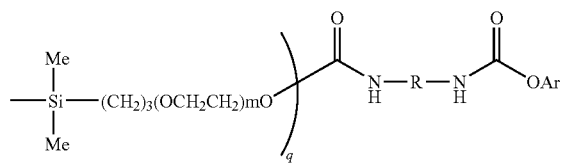

In these generalized adduct structures, all applicable designations are as used in connection with formula I.

As noted above, the thermosetting resin formulations embrace epoxy, episulfide and/or benzoxazine. Representative epoxy monomers contemplated for use herein the preparation of invention toughening agents include bisphenol F diglycidyl ether, bisphenol A diglycidyl ether, 4-vinyl-1-cyclohexene diepoxide, butanediol diglycidyl ether, neopentylglycol diglycidyl ether, 3,4-epoxycyclohexylmethyl-3,4-epoxycyclohexanecarboxylate, limonene diepoxide, hexanediol diglycidyl ether, trimethylolpropane triglycidyl ether, aniline diglycidyl ether, diglycidyl ether of propylene glycol, cyanuric acid triglycidyl ether, ortho-phthalic acid diglycidyl ether, diglycidyl ester of linoleic dimer acid, dicyclopentadiene diepoxide, diglycidyl ether of tetrachloro bisphenol A, 1,1,1-tris(p-hydroxyphenyl)ethane glycidyl ether, tetra glycidyl ether of tetrskis(4-hydroxyphenyl) ethane, epoxy phenol novolac resins, epoxy cresol novolac resins, tetraglycidyl-4,4'-diaminodiphenylmethane, and the like.

Among the commercially available epoxy resins suitable for use herein are polyglycidyl derivatives of phenolic compounds, such as those available under the tradenames EPON 828, EPON 1001, EPON 1009, and EPON 1031, from Shell Chemical Co.; DER 331, DER 332, DER 334, and DER 542 from Dow Chemical Co.; GY285 from Ciba Specialty Chemicals, Tarrytown, N.Y.; and BREN-S from Nippon Kayaku, Japan. Other suitable epoxy resins include polyepoxides prepared from polyols and the like and polyglycidyl derivatives of phenol-formaldehyde novolacs, the latter of which are available commercially under the tradenames DEN 431, DEN 438, and DEN 439 from Dow Chemical Company. Cresol analogs are also available commercially ECN 1235, ECN 1273, and ECN 1299 from Ciba Specialty Chemicals. SU-8 is a bisphenol A-type epoxy novolac available from Resolution. Polyglycidyl adducts of amines, aminoalcohols and polycarboxylic acids are also useful in this invention, commercially available resins of which include GLYAMINE 135, GLYAMINE 125, and GLYAMINE 115 from F.I.C. Corporation; ARALDITE MY-720, ARALDITE MY-721, ARALDITE 0500, and ARALDITE 0510 from Ciba Specialty Chemicals and PGA-X and PGA-C from the Sherwin-Williams Co. And of course combinations of the different epoxy resins are also desirable for use herein.

Representative episulfide monomers for use herein are the thiirane counterparts to the epoxy monomers noted in the preceding paragraphs.

Representative benzoxazine monomers for use herein include those embraced by the following structure:

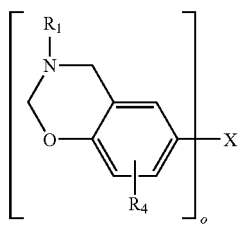

BOZ-A where o is 1-4, X is selected from a direct bond (when o is 2), alkyl (when o is 1), alkylene (when o is 2-4), carbonyl (when o is 2), thiol (when o is 1), thioether (when o is 2), sulfoxide (when o is 2), and sulfone (when o is 2), $R_1$ is selected from hydrogen, alkyl, alkenyl and aryl, and $R_4$ is selected from hydrogen, halogen, alkyl and alkenyl.

Alternatively, the benzoxazine may be embraced by the following structure:

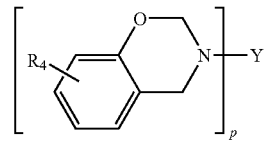

BOZ-B where p is 2, Y is selected from biphenyl (when p is 2), diphenyl methane (when p is 2), diphenyl isopropane (when p is 2), diphenyl sulfide (when p is 2), diphenyl sulfoxide (when p is 2), diphenyl sulfone (when p is 2), and diphenyl ketone (when p is 2), and $R_4$ is selected from hydrogen, halogen, alkyl and alkenyl.

More specifically, within structure BOZ-A the benzoxazine may be embraced by the following structure BOZ-C:

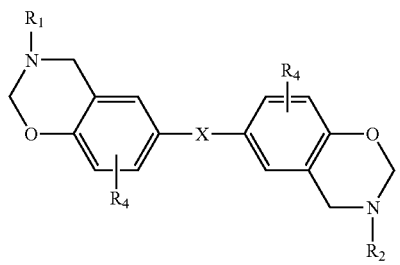

BOZ-C where X is selected from a direct bond, $CH_2$, $C(CH_3)_2$, $C=O$, S, $S=O$ and $O=S=O$, $R_1$ and $R_2$ are the same or different and are selected from hydrogen, alkyl, such as methyl, ethyl, propyls and butyls, alkenyl, such as allyl, and aryl and $R_4$ are the same or different and are selected from hydrogen or alkenyl, such as allyl.

Representative benzoxazines within structure BOZ-C include:

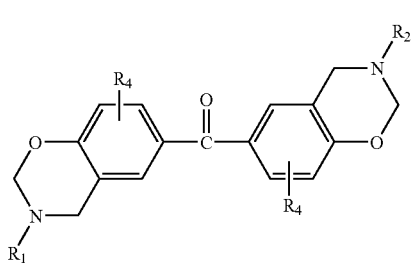

BOZ-D

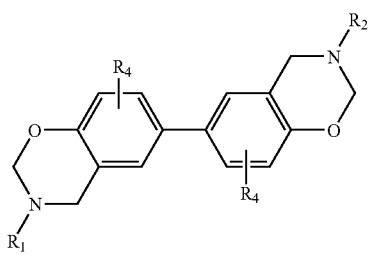

BOZ-E

BOZ-F
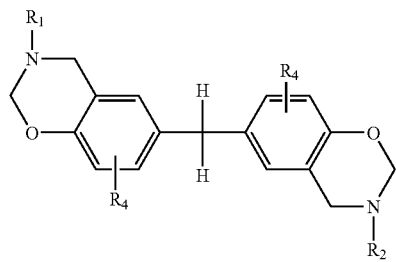
BOZ-G
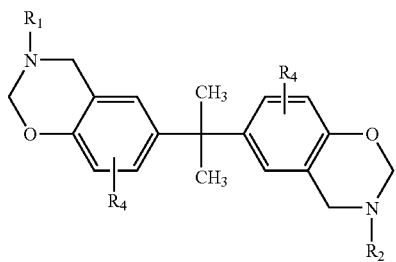
where $R_1$, $R_2$ and $R_4$ are as defined above.
Though not embraced by benzoxazine structures BOZ-A or BOZ-B, additional benzoxazines are within the following structures:
BOZ-H
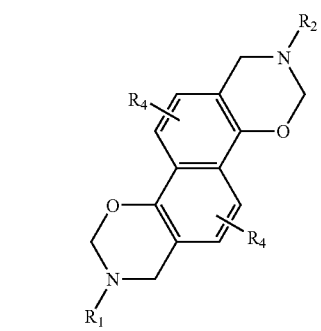
BOZ-I
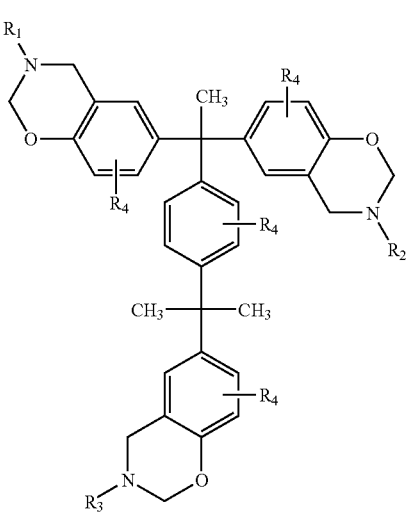
BOZ-J
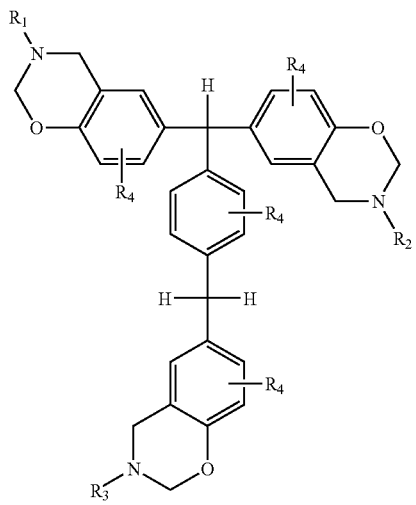
where $R_1$, $R_2$ and $R_4$ are as defined above, and $R_3$ is defined as $R_1$, $R_2$ or $R_4$.
Specific examples of these benzoxazines include:
BOZ-K
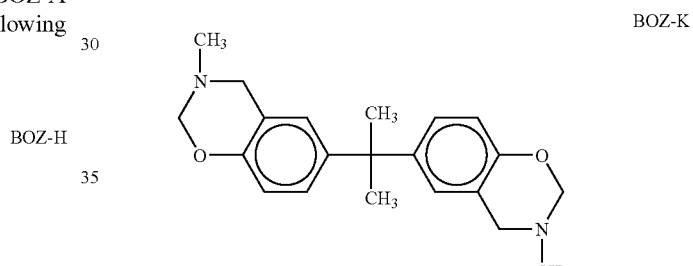
BOZ-L
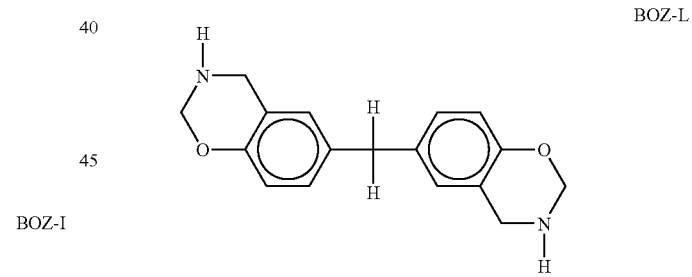
BOZ-M
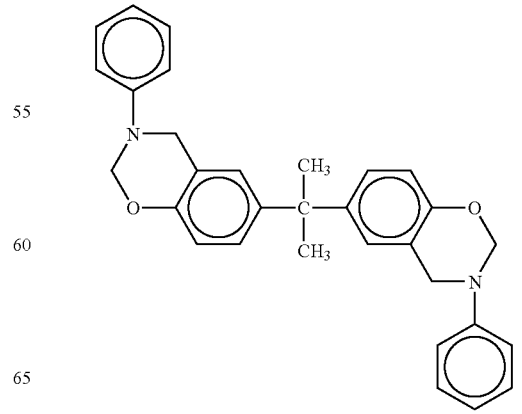

-continued

BOZ-N
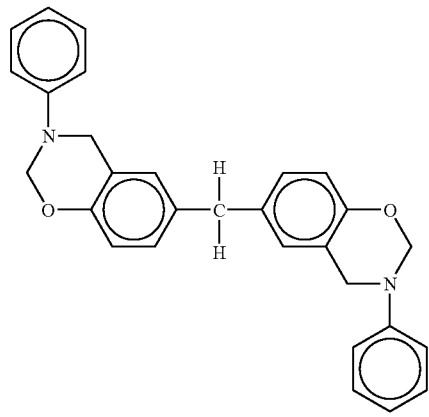

BOZ-O
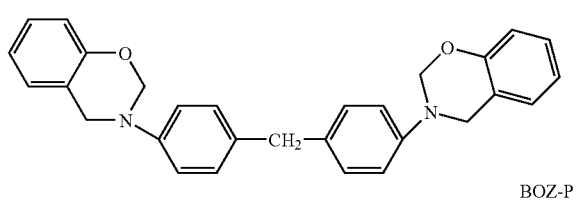

BOZ-P
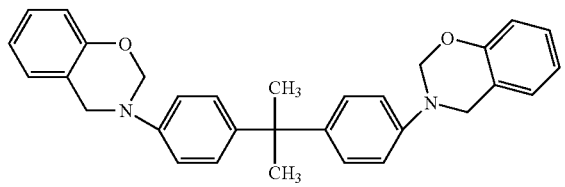

BOZ-Q
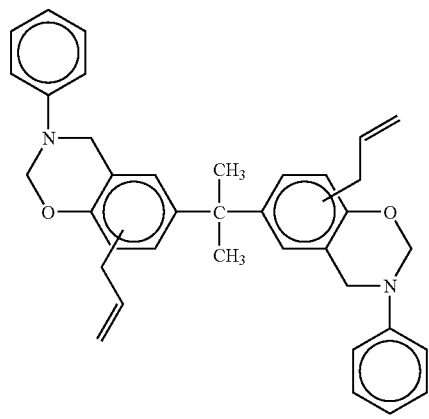

BOZ-R
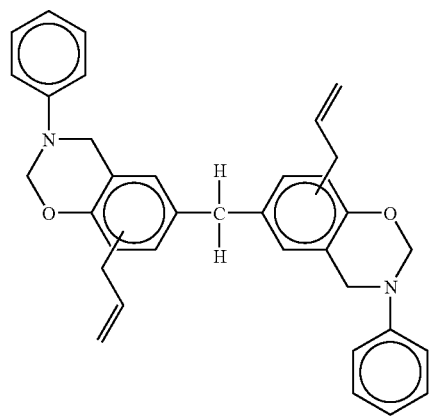

The benzoxazine component may include the combination of multifunctional benzoxazines and monofunctional benzoxazines, or may be the combination of one or more multifunctional benzoxazines or one or more monofunctional benzoxazines.

Examples of monofunctional benzoxazines may be embraced by the following structure:

BOZ-S
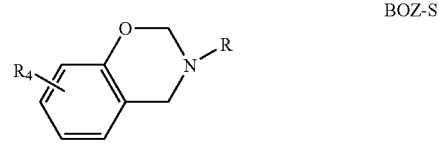

where R is alkyl, such as methyl, ethyl, propyls and butyls, or aryl with or without substitution on one, some or all of the available substitutable sites, and $R_4$ is selected from hydrogen, halogen, alkyl and alkenyl.

For instance, monofunctional benzoxazines may be embraced by the structure

BOZ-T
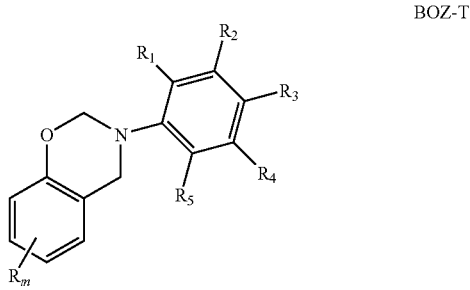

where in this case R is selected from alkyl, alkenyl, each of which being optionally substituted or interrupted by one or more O, N, S, C=O, COO, and NHC=O, and aryl; m is 0-4; and $R_1$-$R_5$ are independently selected from hydrogen, alkyl, alkenyl, each of which being optionally substituted or interrupted by one or more O, N, S, C=O, COOH, and NHC=O, and aryl.

Specific examples of such a monofunctional benzoxazine are:

BOZ-U
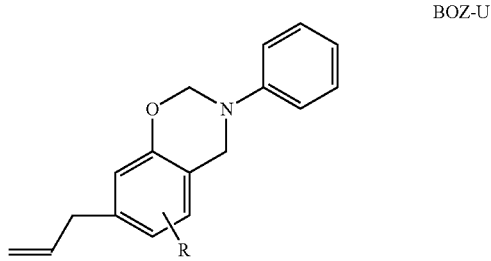

where R is as defined above; or

BOZ-V
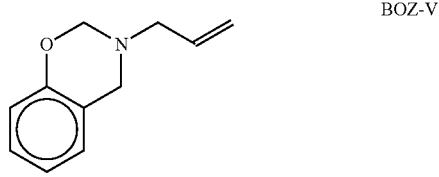

Many benzoxazines are presently available commercially from several sources, including Huntsman Advanced Materials; Georgia-Pacific Resins, Inc.; and Shikoku Chemicals Corporation, Chiba, Japan, the last of which offers among others B-a, B-m, F-a, C-a, Pd and F-a benzoxazine resins.

If desired, however, instead of using commercially available sources, the benzoxazine may typically be prepared by reacting a phenolic compound, such as a bisphenol A, bisphenol F, bisphenol S or thiodiphenol, with an aldehyde and an alkyl or aryl amine. U.S. Pat. No. 5,543,516, hereby expressly incorporated herein by reference, describes a method of forming benzoxazines, where the reaction time can vary from a few minutes to a few hours, depending on reactant concentration, reactivity and temperature. See also Burke et al., *J. Org. Chem.*, 30(10), 3423 (1965); see generally U.S. Pat. Nos. 4,607,091 (Schreiber), 5,021,484 (Schreiber), 5,200,452 (Schreiber) and 5,443,911 (Schreiber).

The benzoxazine should be present in the inventive composition in an amount in the range of about 10 to about 90 percent by weight, such as about 25 to about 75 percent by weight, desirably about 35 to about 65 percent by weight, based on the total weight of the composition.

Benzoxazine polymerization can be self-initiated under elevated temperature conditions and also by inclusion of cationic initiators, such as Lewis acids, and other known cationic initiators, such as metal halides; organometallic derivatives; metallophorphyrin compounds such as aluminum phthalocyanine chloride; methyl tosylate, methyl triflate, and triflic acid; and oxyhalides. Likewise, basic materials, such as imidizaoles, may be used to initiate polymerization.

Typically, the composition including the inventive adduct have about 40 to about 95 weight percent of the thermoset component, about 5 to about 50 weight percent of the inventive adduct, and about 0.2 to about 10 weight percent of the curative.

As noted above, the composition may include as the thermoset component any epoxy, episulfide or benzoxazine, at least a portion of which is a multifunctional monomer. Ordinarily, the multifunctional monomer used in the composition should be included in amount within the range of about 20 weight percent to about 100 weight percent of the composition.

A monofunctional monomer, if present, should ordinarily be used as a reactive diluent, or crosslink density modifier. In the event such a monofunctional monomer is included as a portion of the composition, such resin should be employed in an amount of up to about 20 weight percent, based on the composition.

As employed herein, the term "curing agent" or "curative" refers to polymerization promoters, co-curing agents, catalysts, initiators or other additives designed to participate in or promote curing of the adhesive formulation. With respect to epoxide-based adhesive formulations, such curing agents include polymerization promoters and catalysts such as, for example, anhydrides, amines, imidazoles, amides, thiols, carboxylic acids, phenols, dicyandiamide, urea, hydrazine, hydrazide, amino-formaldehyde resins, melamine-formaldehyde resins, amine-boron trihalide complexes, quaternary ammonium salts, quaternary phosphonium salts, tri-aryl sulfonium salts, di-aryl iodonium salts, diazonium salts, and the like, as well as combinations of any two or more thereof, optionally also including a transition metal complex. Presently preferred curing agents and catalysts for epoxy composition include anhydrides, amines, imidazoles, and the like.

As readily recognized by those of skill in the art, curing agents contemplated for use in the practice of the present invention will vary with the reactive functionality(ies) present, the presence of optional co-reactant(s), and the like. Typically, the quantity of curing agent will fall in the range of about 1 weight percent up to about 50 weight percent of the composition, with presently preferred amounts of curing agent falling in the range of about 5 weight percent up to about 40 weight percent of the composition.

Initiators contemplated for use with epoxide-based adhesive formulations include hydroxy functionalized compounds such as, for example, alkylene glycols. Preferred alkylene glycols include ethylene glycols and propylene glycols.

Fillers contemplated for optional use in the practice of the present invention include, for example, aluminum nitride, boron nitride, silicon carbide, diamond, graphite, beryllium oxide, magnesia, silicas, such as fumed silica or fused silica, alumina, perfluorinated hydrocarbon polymers (i.e., TEFLON), thermoplastic polymers, thermoplastic elastomers, mica, glass powder and the like. Preferably, the particle size of these fillers will be about 20 microns. If aluminum nitride is used as a filler, it is preferred that it be passivated via an adherent, conformal coating (e.g., silica, or the like). Some of those fillers may impart properties to the adhesive formulation such as, for example, reduced thermal expansion of the cured adhesive, reduced dielectric constant, improved toughness, increased hydrophobicity, and the like.

Flexibilizers (also called plasticizers) contemplated for optional use in the practice of the present invention include branched polyalkanes or polysiloxanes that lower the $T_g$ of the formulation. Such flexibilizers include, for example, polyethers, polyesters, polythiols, polysulfides, and the like. If used, flexibilizers typically are present in the range of about 0.5 weight percent up to about 30 weight percent of the composition.

Dyes and/or pigments may be used in the practice of the present invention. When present, such dyes and pigments are typically present in the range of about 0.5 weight percent up to about 5 weight percent based on the composition.

Rubber particles, especially rubber particles that have relatively small average particle size (e.g., less than about 500 nm or less than about 200 nm), may also be included in the compositions of the present invention. The rubber particles may or may not have a shell common to known core-shell structures.

In the case of rubber particles having a core-shell structure, such particles generally have a core comprised of a polymeric material having elastomeric or rubbery properties (i.e., a glass transition temperature less than about 0° C., e.g., less than about −30° C.) surrounded by a shell comprised of a non-elastomeric polymeric material (i.e., a thermoplastic or thermoset/crosslinked polymer having a glass transition temperature greater than ambient temperatures, e.g., greater than about 50° C.). For example, the core may be comprised of a diene homopolymer or copolymer (for example, a homopolymer of butadiene or isoprene, a copolymer of butadiene or isoprene with one or more ethylenically unsaturated monomers such as vinyl aromatic monomers, (meth)acrylonitrile, (meth)acrylates, or the like) while the shell may be comprised of a polymer or copolymer of one or more monomers such as (meth)acrylates (e.g., methyl methacrylate), vinyl aromatic monomers (e.g., styrene), vinyl cyanides (e.g., acrylonitrile), unsaturated acids and anhydrides (e.g., acrylic acid), (meth) acrylamides, and the like having a suitably high glass transition temperature. Other rubbery polymers may also be suitably be used for the core, including polybutylacrylate or polysiloxane elastomer (e.g., polydimethylsiloxane, particularly crosslinked polydimethylsiloxane).

The rubber particle may be comprised of more than two layers (e.g., a central core of one rubbery material may be surrounded by a second core of a different rubbery material or the rubbery core may be surrounded by two shells of different composition or the rubber particle may have the structure soft core, hard shell, soft shell, hard shell). In one embodiment of the invention, the rubber particles used are comprised of a core and at least two concentric shells having different chemical compositions and/or properties. Either the core or the shell or both the core and the shell may be crosslinked (e.g., ionically or covalently). The shell may be grafted onto the core. The polymer comprising the shell may bear one or more different types of functional groups (e.g., epoxy groups) that are capable of interacting with other components of the compositions of the present invention.

Typically, the core will comprise from about 50 to about 95 weight percent of the rubber particles while the shell will comprise from about 5 to about 50 weight percent of the rubber particles.

Preferably, the rubber particles are relatively small in size. For example, the average particle size may be from about 0.03 to about 2 microns or from about 0.05 to about 1 micron. The rubber particles may have an average diameter of less than about 500 nm, such as less than about 200 nm. For example, the core-shell rubber particles may have an average diameter within the range of from about 25 to about 200 nm.

Methods of preparing rubber particles having a core-shell structure are well-known in the art and are described, for example, in U.S. Pat. Nos. 4,419,496, 4,778,851, 5,981,659, 6,111,015, 6,147,142 and 6,180,693, each of which being incorporated herein by reference in its entirety.

Rubber particles having a core-shell structure may be prepared as a masterbatch where the rubber particles are dispersed in one or more epoxy resins such as a diglycidyl ether of bisphenol A. For example, the rubber particles typically are prepared as aqueous dispersions or emulsions. Such dispersions or emulsions may be combined with the desired epoxy resin or mixture of epoxy resins and the water and other volatile substances removed by distillation or the like. One method of preparing such masterbatches is described in more detail in International Patent Publication No. WO 2004/108825, incorporated herein by reference in its entirety. For example, an aqueous latex of rubber particles may be brought into contact with an organic medium having partial solubility in water and then with another organic medium having lower partial solubility in water than the first organic medium to separate the water and to provide a dispersion of the rubber particles in the second organic medium. This dispersion may then be mixed with the desired epoxy resin(s) and volatile substances removed by distillation or the like to provide the masterbatch.

Particularly suitable dispersions of rubber particles having a core-shell structure in an epoxy resin matrix are available from Kaneka Corporation.

For instance, the core may be formed predominantly from feed stocks of polybutadiene, polyacrylate, polybutadiene/acrylonitrile mixture, polyols and/or polysiloxanes or any other monomers that give a low glass transition temperature. The outer shells may be formed predominantly from feed stocks of polymethylmethacrylate, polystyrene or polyvinyl chloride or any other monomers that give a higher glass transition temperature.

The core shell rubbers may have a particle size in the range of 0.07 to 10 um, such as 0.1 to 5 um.

The core shell rubber made in this way are may be dispersed in an epoxy matrix or a phenolic matrix. Examples of epoxy matrices include the diglycidyl ethers of bisphenol A, F or S, or biphenol, novalac epoxies, and cycloaliphatic epoxies. Examples of phenolic resins include bisphenol-A based phenoxies.

The core shell rubber dispersion may be present in the epoxy or phenolic matrix in an amount in the range of about 5 to about 50% by weight, with about 15 to about 25% by weight being desirable based on viscosity considerations.

When used in the inventive compositions, these core shell rubbers allow for toughening to occur in the composition and oftentimes in a predictable manner—in terms of temperature neutrality toward cure—because of the substantial uniform dispersion, which is ordinarily observed in the core shell rubbers as they are offered for sale commercially.

Many of the core-shell rubber structures available from Kaneka are believed to have a core made from a copolymer of (meth)acrylate-butadiene-styrene, where the butadiene is the primary component in the phase separated particles, dispersed in epoxy resins. Other commercially available masterbatches of core-shell rubber particles dispersed in epoxy resins include GENIOPERL M23A (a dispersion of 30 weight percent core-shell particles in an aromatic epoxy resin based on bisphenol A diglycidyl ether; the core-shell particles have an average diameter of ca. 100 nm and contain a crosslinked silicone elastomer core onto which an epoxy-functional acrylate copolymer has been grafted); the silicone elastomer core represents about 65 weight percent of the core-shell particle), available from Wacker Chemie GmbH.

In the case of those rubber particles that do not have such a shell, the rubber particles may be based on the core of such structures.

Preferably, the rubber particles are relatively small in size. For example, the average particle size may be from about 0.03 to about 2μ or from about 0.05 to about 1μ. In certain embodiments of the invention, the rubber particles have an average diameter of less than about 500 nm. In other embodiments, the average particle size is less than about 200 nm. For example, the rubber particles may have an average diameter within the range of from about 25 to about 200 nm or from about 50 to about 150 nm.

The rubber particles generally are comprised of a polymeric material having elastomeric or rubbery properties (i.e., a glass transition temperature less than about 0° C., e.g., less than about −30° C.). For example, the rubber particles may be comprised of a diene homopolymer or copolymer (for example, a homopolymer of butadiene or isoprene, a copolymer of butadiene or isoprene with one or more ethylenically unsaturated monomers such as vinyl aromatic monomers, (meth)acrylonitrile, (meth)acrylates, or the like) and polysiloxanes. The rubber particles may contain functional groups such as carboxylate groups, hydroxyl groups or the like and may have a linear, branched, crosslinked, random copolymer or block copolymer structure.

For instance, the rubber particles may be formed predominantly from feed stocks of dienes such as butadiene, (meth)acrylates, ethylenically unsaturated nitriles such as acrylonitrile, and/or any other monomers that when polymerized or copolymerized yield a polymer or copolymer having a low glass transition temperature.

The rubber particles may be used in a dry form or may be dispersed in a matrix, such as an epoxy matrix or a phenolic matrix. The matrix material preferably is liquid at room temperature. Examples of epoxy matrices include the diglycidyl ethers of bisphenol A, F or S, or bisphenol, novalac epoxies, and cycloaliphatic epoxies. Examples of phenolic resins include bisphenol-A based phenoxies.

The rubber particles may be present in the epoxy or phenolic matrix in an amount in the range of about 5 to about 50 weight percent (about 15 to about 40 weight percent).

Typically, the composition may contain from about 5 to about 35 weight percent (in one embodiment, from about 15 to about 30 weight percent) rubber particles.

Combinations of different rubber particles may advantageously be used in the present invention. The rubber particles may differ, for example, in particle size, the glass transition temperatures of their respective materials, whether, to what extent and by what the materials are functionalized, and whether and how their surfaces are treated.

A portion of the rubber particles may be supplied to the adhesive composition in the form of a masterbatch wherein the particles are stably dispersed in an epoxy resin matrix and another portion may be supplied to the adhesive composition in the form of a dry powder (i.e., without any epoxy resin or other matrix material). For example, the adhesive composition may be prepared using both a first type of rubber particles in dry powder form having an average particle diameter of from about 0.1 to about 0.5μ and a second type of rubber particles stably dispersed in a matrix of liquid bisphenol A diglycidyl ether at a concentration of from about 5 to about 50 percent by weight having an average particle diameter of from about 25 to about 200 nm. The weight ratio of first type:second type rubber particles may be from about 1.5:1 to about 0.3:1, for example.

The chemical composition of the rubber particles may be essentially uniform throughout each particle. However, the outer surface of the particle may be modified by reaction with a coupling agent, oxidizing agent or the like so as to enhance the ability to disperse the rubber particles in the adhesive composition (e.g., reduce agglomeration of the rubber particles, reduce the tendency of the rubber particles to settle out of the adhesive composition). Modification of the rubber particle surface may also enhance the adhesion of the epoxy resin matrix to the rubber particles when the adhesive is cured. The rubber particles may alternatively be irradiated so as to change the extent of crosslinking of the polymer(s) constituting the rubber particles in different regions of the particle. For example, the rubber particles may be treated with gamma radiation such that the rubber is more highly crosslinked near the surface of the particle than in the center of the particle.

Rubber particles that are suitable for use in the present invention are available from commercial sources. For example, rubber particles supplied by Eliokem, Inc. may be used, such as NEP R0401 and NEP R401S (both based on acrylonitrile/butadiene copolymer); NEP R0501 (based on carboxylated acrylonitrile/butadiene copolymer; CAS No. 9010-81-5); NEP R0601A (based on hydroxy-terminated polydimethylsiloxane; CAS No. 70131-67-8); and NEP R0701 and NEP 0701S (based on butadiene/styrene/2-vinylpyridine copolymer; CAS No. 25053-48-9).

Rubber particles that have been treated with a reactive gas or other reagent to modify the outer surfaces of the particles by, for instance, creating polar groups (e.g., hydroxyl groups, carboxylic acid groups) on the particle surface, are also suitable for use in the present invention. Illustrative reactive gases include, for example, ozone, $Cl_2$, $F_2$, $O_2$, $SO_3$, and oxidative gases. Methods of surface modifying rubber particles using such reagents are known in the art and are described, for example, in U.S. Pat. Nos. 5,382,635; 5,506,283; 5,693,714; and 5,969,053, each of which is incorporated herein by reference in its entirety. Suitable surface modified rubber particles are also available from commercial sources, such as the rubbers sold under the tradename VISTAMER by Exousia Corporation.

Where the rubber particles are initially provided in dry form, it may be advantageous to ensure that such particles are well dispersed in the adhesive composition prior to curing the adhesive composition. That is, agglomerates of the rubber particles are preferably broken up so as to provide discrete individual rubber particles, which may be accomplished by intimate and thorough mixing of the dry rubber particles with other components of the adhesive composition. For example, dry rubber particles may be blended with epoxy resin and milled or melt compounded for a length of time effective to essentially completely disperse the rubber particles and break up any agglomerations of the rubber particles.

Conditions suitable to cure the inventive compositions include exposing the compositions to a temperature of at least about 120° C. but less than about 190° C. for about 0.5 up to about 60 minutes, such as 30 minutes at 180° C.

More specifically, the inventive adducts may be used as latent curatives for the thermoset, if they contain a thiol and/or amine functional group or if they are reacted to become functionalized with such a group. In addition, they may be used to prepare compositions capable of curing at temperatures lower than those set forth above, such as at about 100° C.

The inventive compositions may also be formulated as one part compositions or two part compositions, as desired. In a one part composition, it may be desirable to grind the inventive adduct to a uniform particle size, such as by cryogenic grinding techniques, to ensure a dispersable particle size. In a two part composition, the inventive adduct may be solubilized in one of the parts.

Adducts E, G, K, N, T and V are already functionalized with amine groups and thus may be used as is without further reaction, for instance. Adduct Q, being functionalized with isocyanates, need only react with an amino alcohol or a hydroxyl thiol, for instance, to functionalize Adduct Q with an amine or thiol, respectively (see below Adduct QA). Adduct B, being hydroxyl functionalized, is first reacted with isocyanate (such as any of those disclosed herein) and then with an amino alcohol or a hydroxyl thiol, for instance, to functionalize Adduct B with an amine or thiol, respectively (see below Adduct BA).

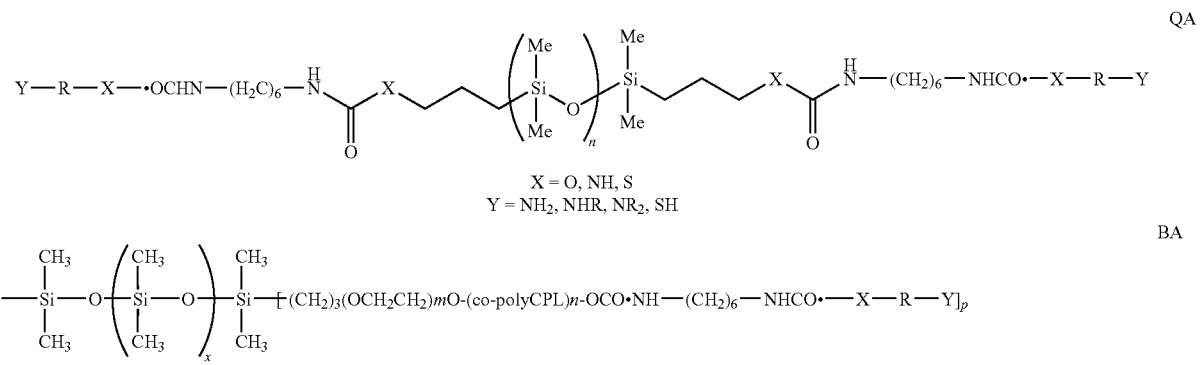

The present invention provides methods for adhesively attaching a first article to a second article. Such methods include (a) applying an inventive composition to a first article, (b) bringing together the first article and a second article into intimate contact to form an assembly, where the first article and the second article are separated only by the adhesive composition applied in step (a), and thereafter, (c) subjecting the assembly to conditions suitable to cure the composition.

In accordance with yet another embodiment of the present invention, there are provided assemblies produced by these methods.

The invention will now be illustrated by way of the following examples.

EXAMPLES

Example 1

General Preparation of Polyurethane Type Adducts

One equivalent of a functionalized polyether or polydimethyl siloxane backbone material (such as one terminated at each end with one of hydroxyl, amino, mercapto or carboxyl) is reacted with 2 equivalents of a diisocyanate (e.g., hexamethylene diisocyanate or isophorone diisocyanate) by bringing into contact the two materials with or without the presence of a chain extender such as trimethylol propane, under appropriate catalysis at a temperature between 20 and 100° C., particularly between 60-80° C., under an inert atmosphere. The reaction is maintained until the isocyanate content indicates a value which indicates complete reaction. The materials may be used individually or in blends in this reaction.

The above intermediate isocyanate terminated adduct is then capped by reaction of the terminal isocyanate functional groups with the required capping agent, such as a phenol (e.g., 2,2'-diallyl bisphenol A or resorcinol), a diamine (e.g., JEFFAMINE D-2000 or HYCAR 1300X21) or an epoxy (e.g., the blend of EPON 828/EPON 1001).

In this manner Adducts A1-2, C1-6, R1-4, S, T, W, Z, AB and AC may be synthesised.

In the case of Adducts D1-D8 an isocyanate-free synthesis route is employed whereby a diamino terminated PDMS material is reacted with 2 equivalents of a CBC-blocked JEFFAMINE to afford the corresponding CBC-terminated adduct. This is then capped by reaction of the terminal CBC groups with an appropriate phenolic capping agent.

Example 2

Preparation of an A-B-A Block Copolymer Type Adduct

Here, one equivalent of a functionalized polyether or polydimethyl siloxane backbone material (such as one terminated at each end with one of hydroxyl, anhydride, (meth)acrylate, or amine) as a Block B is reacted with an appropriate amount (2 equivalents for example) of a Block A material such as:

Reaction of amino/mercapto/hydroxy terminated Block B material with a lactone such as caprolactone [Adducts B1-4], Reaction of an amine- or mercapto-containing material by Michael addition reaction of one or more equivalents of a JEFFAMINE onto an acrylate [Adducts K1-10] or methacrylate [Adducts N1-9] terminated Block B material, or reaction of an amine- or mercapto-terminated Block B material by Michael addition reaction onto a (meth)acrylate-terminated Block A segment [Adduct Y], or Reaction of an anhydride terminated Block B material with one or more equivalents of an amine/mercapto/hydroxy terminated Block A material [Adduct E]

The Block A and B materials in proper stoichiometric amounts are heated to an appropriate temperature for a period of time of 1-24 hours, depending on the nature and identity of the reactants, to form the an A-B-A block copolymer type adduct.

Example 3

Capping of Amine Terminated Adducts with Epoxy Groups

This reaction was carried out generally according to U.S. Pat. No. 5,084,532. Thus, a blend of EPON 828 and EPON 1001 in appropriate molar ratios was placed into a reaction vessel and heated with mechanical stirring at a temperature of 110° C. for a period of time sufficient to create a flowable melted epoxy blend. JEFFAMINE T-403 was then added dropwise and the reaction allowed to stir for a period of time of 1 hour at a temperature of 110° C. An appropriate amine terminated adduct was then added dropwise to this reaction mixture, and the reaction was stirred for a further 1 hour period of time at the same temperature, and then allowed to cool to room temperature.

Adducts F, H, M1-10, P1-9, and W were prepared according to this procedure.

Example 4

Capping of Amine Terminated Adducts with CBC

This reaction was carried out generally with reference to Angew. Chem. Int. Ed., 42, 5094-5097 (2003).

An amine terminated adduct and an appropriate required amount of carbonyl biscaprolactam are placed into a reaction vessel, heated with stirring to a temperature of 100-150° C. for a period of time of between 1-24 hours and then allowed to cool.

Adducts I, J, L1-9, O1-7, U1, X, AD1-3 and AE were prepared according to this procedure.

Example 5

An adduct exhibiting good low temperature wedge impact toughening properties was prepared by a Michael addition reaction of JEFFAMINE D-2000 onto the methacrylate double bond of a (meth)acrylate-terminated polydimethyl siloxane, DMS R11. The initial amine-terminated Michael adduct (Adducts K1-10, N1-9) was then capped by reaction with carbonyl biscaprolactam (Adducts L1-9, O1-7) or epoxy (Adducts P1-9, M1-10) as depicted in the following scheme and as described in Examples 3 and 4 previously:

temperature. The initial adduct (Adduct N7) was obtained as a yellow, silk-like low viscosity resin.

To cap with CBC, the resin obtained above (37.88 g, 0.0075 mol) was mixed with carbonyl biscaprolactam (3.78 g, 0.015 mol), deaerated under vacuum, flushed with inert gas and heated at a temperature of 100° C. for a period of time of 90 minutes. The reaction was allowed to cool to room temperature to afford a yellow, gel-like/semi-solid resin (Adduct O7).

Alternatively, to cap with epoxy, a reaction was carried out generally in accordance with U.S. Pat. No. 5,084,532 (Schenkel), such as in Example 1 thereof.

To cap with phenol instead, a reaction was carried out as described below in the following paragraph, which describes a one-pot synthesis.

Synthesis of Adduct AC with 4:1 Ratio of PPG to PDMS

In a clean, dry round bottom flask equipped with a mechanical overhead stirrer, nitrogen inlet, thermometer and a pressure equalising dropping funnel was charged PPG 2000 (120 g, 0.06 mol), silanol DMS C16 (10.875 g, 0.015 mol), trimethylol propane (0.76 g, 0.0056 mol) and hexamethylene diisocyanate (22.96 g, 0.136 mol). Dibutyl tin dilaurate was added as a catalyst and the solution stirred under an inert atmosphere and the temperature raised to 60° C. at which point reaction is observed to start with the formation of bubbles and an increase in temperature to 80° C.-120° C. The contents were stirred at a temperature of 80-120° C. for a period of time of 90 minutes and then cooled to a temperature

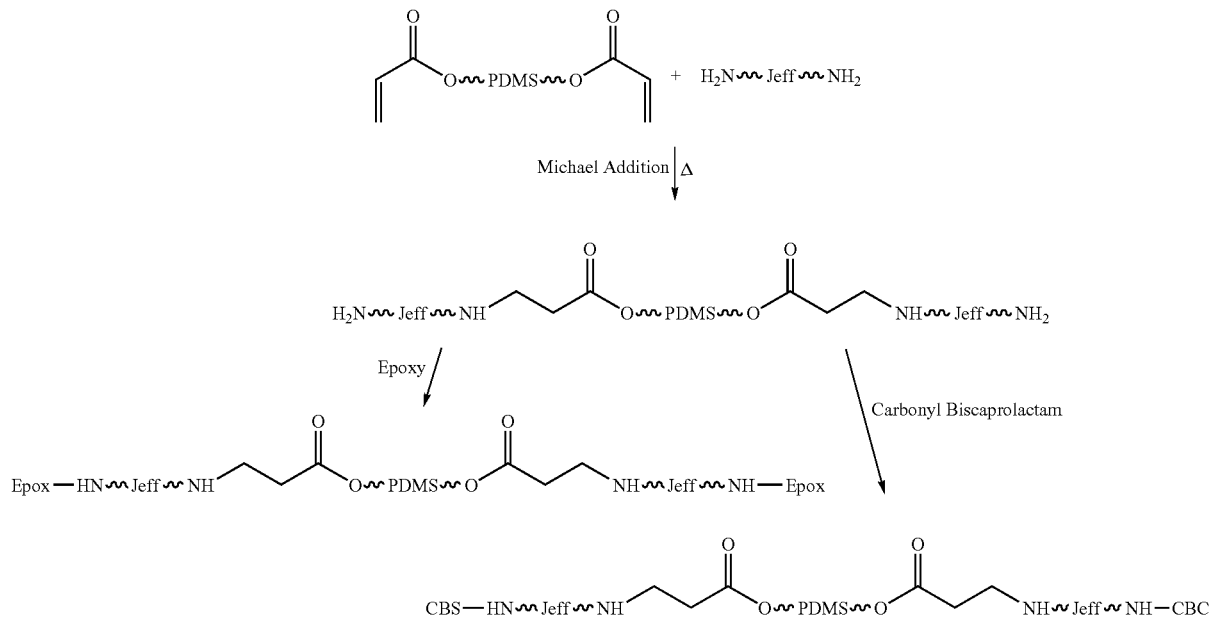

More specifically, in a clean, dry round bottom flask JEFFAMINE D-2000 (80 g, 0.04 mol) was heated to a temperature of 170° C. and (meth)acrylate terminated PDMS, DMS R11 (21 g, 0.02 mol) was added dropwise with stirring. On complete addition of the DMS R11, the reaction was stirred for a further period of 90 minutes before cooling to room of 80-90° C. 2,2'-diallyl bisphenol A was added with stirring continued for a further period of time of 90 minutes, with the final 30 minutes of stirring being performed under reduced pressure to remove volatiles, and then cooled to room temperature. The so-formed adduct is believed to have a structure similar to that shown below:

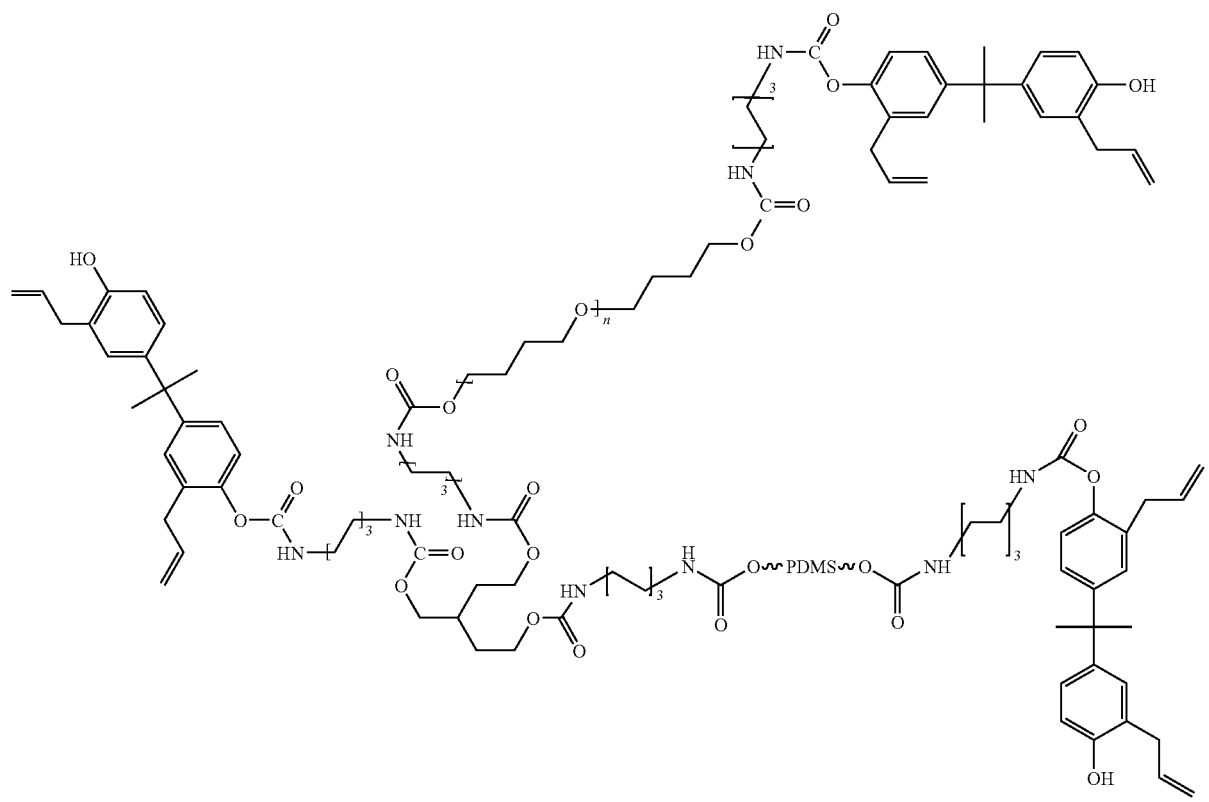

Example 6

Table 1 represents a set of model formulations prepared with different adducts.

TABLE 1

| | | Sample Nos./Amt (wt %) | | | | | |
|---|---|---|---|---|---|---|---|
| | | A | | | | | B |
| Type | Identity | I | II | III | IV | V | |
| Epoxy | EPON 828 | 65 | 60 | 50 | 40 | 30 | 45 |
| Toughener | Adduct | 5 | 10 | 20 | 30 | 20 | 20 |
| | POLYDIS 3614* | 20 | 20 | 20 | 20 | 40 | — |
| | Epoxy-Jeffamine Adduct** | — | — | — | — | — | 20 |
| | CARDOLITE 2513*** | 4 | 4 | 4 | 4 | 4 | 4 |
| Silica Filler | AEROSIL R202 | 4 | 4 | 4 | 4 | 4 | 4 |
| Curative | DICY | 4 | 4 | 4 | 4 | 4 | 4 |
| | FENURON | 0.15 | 0.15 | 0.15 | 0.15 | 0.15 | 0.15 |

*Nitrile rubber modified epoxy prepolymer based on DGEBPA, available commercially from Struktol Company of America, Stow, OH
**Prepared generally in accordance with U.S. Pat. No. 5,084,532 (Schenkel), such as in Example 1 thereof
***Reactive diluent Tables 1A-1E show a list of raw material components used to prepare many of the adducts referred to herein, and presented in the examples which follow.

TABLE 1A

| Adduct | Raw Material |
|---|---|
| A1 | PPG 2000, HMDI, TMP, 2,2'-DABPA |
| A2 | PolyTHF 2000, IPDI, TMP, 2,2'-DABPA |
| B1 | DMS C15, Caprolactone n = 16 |
| B2 | DMS C15, Caprolactone n = 24 |
| B3 | DMS C21, Caprolactone n = 16 |
| B4 | DMS C21, Caprolactone n = 24 |
| C1 | B1 + hexamethylene diisocyanate + 2,2'-diallylbisphenol A |
| C2 | B2 + hexamethylene diisocyanate + 2,2'-diallylbisphenol A |
| C3 | B3 + hexamethylene diisocyanate + 2,2'-diallylbisphenol A |
| C4 | B4 + hexamethylene diisocyanate + 2,2'-diallylbisphenol A |
| C5 | SB 800 + hexamethylene diisocyanate + 2,2'-diallylbisphenol A |
| C6 | SB 801 + hexamethylene diisocyanate + 2,2'-diallylbisphenol A |

TABLE 1B

| Adduct | Raw Material |
|---|---|
| D1 | CBC Capped JEFFAMINE D-400/PDMS 1218/resorcinol |
| D2 | CBC Capped JEFFAMINE D-400/PDMS 1218/2-allyl phenol |
| D3 | CBC Capped JEFFAMINE D-400/PDMS 3345/resorcinol |
| D4 | CBC Capped JEFFAMINE D-400/PDMS 3345/2-allyl phenol |
| D5 | CBC Capped JEFFAMINE D-2000/PDMS 1218/resorcinol |
| D6 | CBC Capped JEFFAMINE D-2000/PDMS 1218/2-allyl phenol |
| D7 | CBC Capped JEFFAMINE D-2000/PDMS 3345/resorcinol |
| D8 | CBC Capped JEFFAMINE D-2000/PDMS 3345/2-allyl phenol |
| E | DMS Z21/JEFFAMINE D-2000 |
| F | E + EPON 828/EPON 1001 |
| G | E @ 150° C. |
| H | G/EPON 828/EPON 1001 |
| I | E + Carbonyl biscaprolactam |
| J | G + Carbonyl biscaprolactam |
| K1 | JEFFAMINE D-2000 + DMS-U22 |

TABLE 1B-continued

| Adduct | Raw Material |
|---|---|
| K2 | JEFFAMINE D-2000 + DBE-U12 |
| K3 | JEFFAMINE D-400 + DBE-U12 |
| K4 | JEFFAMINE D-2000 + TEGOMER V—Si 2250 |
| K5 | JEFFAMINE D-400 + TEGOMER V—Si 2250 |
| K6 | JEFFAMINE D-2000 + DMS U22 |
| K7 | JEFFAMINE D-4000 + DBE U12 |
| K8 | JEFFAMINE D-4000 + TEGOMER V—Si 2250 |
| K9 | JEFFAMINE T-5000 + DBE U12 (2:1) |
| K10 | JEFFAMINE T-5000 + DBE U12 (1:1) |

TABLE 1C

| Adduct | Raw Material |
|---|---|
| L1 | K1 + CBC |
| L2 | K2 + CBC |
| L3 | K3 + CBC |
| L4 | K4 + CBC |
| L5 | JEFFAMINE D-4000 + DBE U12 + CBC |
| L6 | JEFFAMINE D-4000 + DMS U22 + CBC |
| L7 | JEFFAMINE D-4000 + TEGOMER V—Si 2250 + CBC |
| L8 | K9 + CBC |
| L9 | K10 + CBC |
| M1 | K1 + EPON 828/EPON 1001 |
| M2 | K2 + EPON 828/EPON 1001 |
| M3 | K3 + EPON 828/EPON 1001 |
| M4 | K9 + EPON 828/EPON 1001 |
| M5 | K4 + EPON 828/EPON 1001 |
| M6 | K5 + EPON 828/EPON 1001 |
| M7 | DMS U22 + JEFFAMINE D-4000 + EPON 828/EPON 1001 |
| M8 | K7 + EPON 828/EPON 1001 |
| M9 | K8 + EPON 828/EPON 1001 |
| M10 | K10 + EPON 828/EPON 1001 |
| N1 | SLM 446016-15 VP + JEFFAMINE D-2000 |
| N2 | SLM 446016-15 VP + JEFFAMINE D-400 |
| N3 | SLM 446016-15 VP + JEFFAMINE D-4000 |
| N4 | SLM 446016-50 VP + JEFFAMINE D-2000 |
| N5 | SLM 446016-50 VP + JEFFAMINE D-400 |
| N6 | SLM 446016-50 VP + JEFFAMINE D-4000 |
| N7 | DMS-R11 + JEFFAMINE D-2000 |
| N8 | DMS-R11 + JEFFAMINE D-400 |
| N9 | DMS-R11 + JEFFAMINE D-4000 |

TABLE 1D

| Adduct | Raw Material |
|---|---|
| O1 | N1 + CBC |
| O2 | N3 + CBC |
| O3 | N9 + CBC |
| O4 | N4 + CBC |
| O5 | N5 + CBC |
| O6 | N6 + CBC |
| O7 | N7 + CBC |
| P1 | N1 + EPON 828/EPON 1001 |
| P2 | N2 + EPON 828/EPON 1001 |
| P3 | N3 + EPON 828/EPON 1001 |
| P4 | N4 + EPON 828/EPON 1001 |
| P5 | N5 + EPON 828/EPON 1001 |
| P6 | N6 + EPON 828/EPON 1001 |
| P7 | N7 + EPON 828/EPON 1001 |
| P8 | N8 + EPON 828/EPON 1001 |
| P9 | N9 + EPON 828/EPON 1001 |
| R1 | DMS-C15 + HMDI + 2,2'-DABPA |
| R2 | DMS-C15 + HMDI + Resorcinol |
| R3 | DMS-C15 + MDI + 2,2'-DABPA |
| R4 | DMS-C15 + MDI + Resorcinol |
| S | TEGOMER C—Si 2342 + HMDI + EPON 828/1001 |
| T | TEGOMER H—Si 2311, HMDI, JEFFAMINE D-2000 |
| U1 | T + CBC |
| U2 | T + EPON 828/1001 |
| V | TEGOMER C—Si 2342 + HMDI + HYCAR 1300X21 |

TABLE 1D-continued

| Adduct | Raw Material |
|---|---|
| W | V + EPON 828/1001 |
| X | V + CBC |
| Y | VTBN 1300X43 + PDMS 1218 |

TABLE 1E

| Adduct | Raw Material |
|---|---|
| Z | TEGOMER H—Si 2311 + HMDI + EPON 828/1001 |
| AA | Poly-THF-block-poly-CPL + DMS-C21 + 3-glycidoxypropyl trimethoxy silane |
| AB | LP3 + TMP + HMDI + 2,2'-DABPA |
| AC | PPG 2000 + DMS C15 + TMP + HMDI + 2,2'-DABPA |
| AD1 | JEFFAMINE D-2000 + DMS-A12 (10 mol. %) + CBC |
| AD2 | JEFFAMINE D-2000 + DMS-A12 (20 mol. %) + CBC |
| AD3 | JEFFAMINE D-2000 + DMS-A12 (50 mol. %) + CBC |
| AE | JEFFAMINE D-2000 + CBC |

The following legend is useful in connection with Tables 1A-1E above.

PPG 2000=Polypropylene glycol (mol. wt. 2000)

TMP=Trimethylol propane 2,2'-DABPA=2,2'-Diallyl bisphenol A

Poly THF 2000=polytetrahydrofuran (mol. wt. 2000)

IPDI=Isophorone diisocyanate

DMAP=N,N'-dimethylaminopyridine

MDI=HMDI=Hexamethylene diisocyanate

HYCAR 1300X21=amine terminated butadiene-acrylonitrile resin

VTBN 1300X43=vinyl terminated butadiene-acrylonitrile resin

PolyTHF-block-poly-CPL=polytetrahydrofuran-poly-caprolactone block co-polymer

LP3=Liquid polysulphide resin

Silane/Silicone Materials:

From Gelest:

DMS-A12=Bis-(3-aminopropyl) terminated PDMS (mol. wt. 900-1000)

DMS-C15=Hydroxy ethylene oxide propyl terminated PDMS (mol. wt. 1000)

DMS-C21=Hydroxy ethylene oxide propyl terminated PDMS (mol. wt. 4500-5500)

DMS-R11=Methacryloxypropyl terminated PDMS (mol. wt. 900-1200)

DMS-U22=(3-Acryloxy-2-hydroxypropyl) terminated PDMS (mol. wt. 1000-1200)

DBE-U12=Acryloxy terminated ethylene oxide dimethylsiloxane-ethylene oxide ABA block copolymer (mol. wt. 1500-1600)

DMS-Z21=Succinic anhydride terminated PDMS (mol. wt. 600-800)

PDMS 1218=Bis-(3-aminopropyl) terminated PDMS (mol. wt. ~1200)

From Wacker Silicones:

PDMS 1218=Bis-(3-aminopropyl) terminated PDMS (mol. wt. ~1200)

PDMS 3345=Bis-(3-aminopropyl) terminated PDMS (mol. wt. ~3350)

SLM 446016-15 VP=Bis-(methacryloxy)methyl terminated PDMS (mol. wt. ~1,330)

SLM 446016-50 VP=Bis-(methacryloxy)methyl terminated PDMS (mol. wt. ~3,880)

SLM 446200-350 #SB 800=Hydroxy terminated PDMS-co-polycaprolactone copolymer (mol. wt. ~5800)

SLM 446200-350 #SB 801=Hydroxy terminated PDMS-co-polycaprolactone copolymer (mol. wt. ~9030)

From Tego Chemie:

TEGOMER V—Si 2250=Linear acryloxy terminated organo-functional PDMS (mol. wt. ~2500).

TEGOMER C—Si 2342=Linear carboxyl terminated organo-functional PDMS (mol. wt. ~2800).

TEGOMER H—Si 2311=Linear hydroxy terminated organo-functional PDMS (mol. wt. ~2500).

The results of the formulation evaluations are set forth below in each of Tables 2-14.

In Tables 2-14, Adducts AC, V, H, U1, U2, M1, M2, M3, M4, M5, N, O1, O2, and O3, respectively, have been evaluated on grit blasted mild steel impact peel test coupons of a 0.8 mm thickness in accordance with ISO 11343, using a bondline thickness of 0.25 mm for wedge impact performance at least one of room temperature, −20° C. and −40° C., for dynamic resistance and impact energy.

TABLE 2

| Wedge Impact @ | | AC-I | AC-II | AC-III | AC-IV | AC-V | B |
|---|---|---|---|---|---|---|---|
| Room Temperature | Dynamic Resistance (N/mm) | — | — | 17.67 | 28.85 | 18.69 | 23.11 |
| −20° C. | | — | — | 7.29 | 17.13 | 7.52 | 18.68 |
| −40° C. | | — | — | — | 2.75 | — | 2.14 |
| Room Temperature | Impact Energy (Joules) | — | — | 5.87 | 9.57 | 5.94 | 7.66 |
| −20° C. | | — | — | 1.91 | 4.89 | 1.91 | 5.67 |
| −40° C. | | — | — | — | 0.63 | — | 0.49 |

Sample Nos. A

TABLE 3

| Wedge Impact @ | | U1-I | U1-II | U1-III | U1-IV | U1-V | B |
|---|---|---|---|---|---|---|---|
| Room Temperature | Dynamic Resistance (N/mm) | — | — | — | 7.78 | — | — |
| −20° C. | | — | — | — | — | — | — |
| −40° C. | | — | — | — | — | — | — |
| Room Temperature | Impact Energy (Joules) | — | — | — | 2.01 | — | — |
| −20° C. | | — | — | — | — | — | — |
| −40° C. | | — | — | — | — | — | — |

Sample Nos. A

TABLE 4

| Wedge Impact @ | | H-I | H-II | H-III | H-IV | H-V | B |
|---|---|---|---|---|---|---|---|
| Room Temperature | Dynamic Resistance (N/mm) | — | — | 1.60 | — | — | — |
| −20° C. | | — | — | — | — | — | — |
| −40° C. | | — | — | — | — | — | — |
| Room Temperature | Impact Energy (Joules) | — | — | 0.39 | — | — | — |
| −20° C. | | — | — | — | — | — | — |
| −40° C. | | — | — | — | — | — | — |

Sample Nos. A

TABLE 5

| Wedge Impact @ | | U2-I | U2-II | U2-III | U2-IV | U2-V | B |
|---|---|---|---|---|---|---|---|
| Room Temperature | Dynamic Resistance (N/mm) | — | — | — | 6.82 | — | — |
| −20° C. | | — | — | — | — | — | — |
| −40° C. | | — | — | — | — | — | — |
| Room Temperature | Impact Energy (Joules) | — | — | — | 1.90 | — | — |
| −20° C. | | — | — | — | — | — | — |
| −40° C. | | — | — | — | — | — | — |

Sample Nos. A

TABLE 6

| Wedge Impact @ | | M1-I | M1-II | M1-III | M1-IV | M1-V | B |
|---|---|---|---|---|---|---|---|
| Room Temperature | Dynamic Resistance (N/mm) | 9.46 | 8.43 | 17.55 | 21.52 | 27.85 | 11.94 |
| −20° C. | | — | — | — | — | — | — |
| −40° C. | | — | — | — | — | — | — |
| Room Temperature | Impact Energy (Joules) | 2.40 | 2.10 | 5.27 | 6.51 | 8.81 | 3.36 |
| −20° C. | | — | — | — | — | — | — |
| −40° C. | | — | — | — | — | — | — |

Sample Nos. A

TABLE 7

| Wedge Impact @ | | M2-I | M2-II | M2-III | M2-IV | M2-V | B |
|---|---|---|---|---|---|---|---|
| Room Temperature | Dynamic Resistance (N/mm) | — | — | 9.81 | 17.49 | 17.65 | 3.16 |
| −20° C. | | — | — | 3.62 | 3.62 | — | — |
| −40° C. | | — | — | — | — | — | — |
| Room Temperature | Impact Energy (Joules) | — | — | 2.65 | 5.14 | 5.17 | 0.82 |
| −20° C. | | — | — | 0.82 | 0.82 | — | — |
| −40° C. | | — | — | — | — | — | — |

Sample Nos. A

TABLE 8

| Wedge Impact @ | | M8-I | M8-II | M8-III | M8-IV | M8-V | B |
|---|---|---|---|---|---|---|---|
| Room Temperature | Dynamic Resistance (N/mm) | — | — | — | — | 4.76 | — |
| −20° C. | | — | — | — | — | — | — |
| −40° C. | | — | — | — | — | — | — |
| Room Temperature | Impact Energy (Joules) | — | — | — | — | 1.24 | — |
| −20° C. | | — | — | — | — | — | — |
| −40° C. | | — | — | — | — | — | — |

TABLE 9

| Wedge Wedge Impact @ | | M4-I | M4-II | M4-III | M4-IV | M4-V | B |
|---|---|---|---|---|---|---|---|
| Room Temperature | Dynamic Resistance (N/mm) | — | — | — | 12.13 | — | — |
| −20° C. | | — | — | — | — | — | — |
| −40° C. | | — | — | — | — | — | — |
| Room Temperature | Impact Energy (Joules) | — | — | — | 3.27 | — | — |
| −20° C. | | — | — | — | — | — | — |
| −40° C. | | — | — | — | — | — | — |

TABLE 10

| Wedge Impact @ | | M5-I | M5-II | M5-III | M5-IV | M5-V | B |
|---|---|---|---|---|---|---|---|
| Room Temperature | Dynamic Resistance (N/mm) | 0 | 5.03 | 18.81 | 15.19 | 19.14 | 14.84 |
| −20° C. | | — | — | 00 | — | 3.21 | — |
| −40° C. | | — | — | — | — | — | — |
| Room Temperature | Impact Energy (Joules) | 0 | 1.37 | 5.77 | 4.58 | 6.14 | 4.13 |
| −20° C. | | — | — | 00 | — | 0.81 | — |
| −40° C. | | — | — | — | — | — | — |

The 00 indicates that the bonds created were evaluated but could be pulled apart manually, i.e., they had zero or 0.00 strength.

TABLE 11

| Wedge Impact @ | | N6-I | N6-II | N6-III | N6-IV | N6-V | B |
|---|---|---|---|---|---|---|---|
| Room Temperature | Dynamic Resistance (N/mm) | — | — | — | 7.77 | — | — |
| −20° C. | | — | — | — | — | — | — |
| −40° C. | | — | — | — | — | — | — |
| Room Temperature | Impact Energy (Joules) | — | — | — | 1.74 | — | — |
| −20° C. | | — | — | — | — | — | — |
| −40° C. | | — | — | — | — | — | — |

TABLE 12

| Wedge Impact @ | | O1-I | O1-II | O1-III | O1-IV | O1-V | B |
|---|---|---|---|---|---|---|---|
| Room Temperature | Dynamic Resistance (N/mm) | — | 4.50 | 10.40 | 8.74 | — | — |
| −20° C. | | — | — | — | — | — | — |
| −40° C. | | — | — | — | — | — | — |
| Room Temperature | Impact Energy (Joules) | — | 1.10 | 2.69 | 2.30 | — | — |
| −20° C. | | — | — | — | — | — | — |
| −40° C. | | — | — | — | — | — | — |

TABLE 13

| Wedge Impact @ | | O7-I | O7-II | O7-III | O7-IV | O7-V | B |
|---|---|---|---|---|---|---|---|
| Room Temperature | Dynamic Resistance (N/mm) | — | — | 17.38 | 21.52 | 17.53 | 20.53 |
| −20° C. | | — | — | 00 | 5.22 | 00 | 7.88 |
| −40° C. | | — | — | — | — | 00 | 1.05 |
| Room Temperature | Impact Energy (Joules) | — | — | 5.49 | 7.01 | 5.47 | 6.81 |
| −20° C. | | — | — | 00 | 1.21 | 00 | 2.00 |
| −40° C. | | — | — | — | — | 00 | 0.22 |

TABLE 14

| Wedge Impact @ | | O3-I | O3-II | O3-III | O3-IV | O3-V | B |
|---|---|---|---|---|---|---|---|
| Room Temperature | Dynamic Resistance (N/mm) | — | — | — | 7.34 | — | — |
| −20° C. | | — | — | — | — | — | — |
| −40° C. | | — | — | — | — | — | — |
| Room Temperature | Impact Energy (Joules) | — | — | — | 1.73 | — | — |
| −20° C. | | — | — | — | — | — | — |
| −40° C. | | — | — | — | — | — | — |

Example 7

Adduct AE-1 was used to formulate epoxy compositions in the amount noted below in Table 15.

TABLE 15

| Composition | | Sample No./Amt. (wt %) | | | | |
|---|---|---|---|---|---|---|
| Type | Identity | 100 | 101 | 102 | 103 | 104 |
| Epoxy | EPON 828 | 80 | 70 | 60 | 50 | 40 |
| Adduct | Adduct AE-1 | — | 10 | 20 | 30 | 40 |
| Epoxy Diluent | CARDOLITE 2513 | 4 | 4 | 4 | 4 | 4 |
| Silica Filler | AEROSIL R202 | 2 | 2 | 2 | 2 | 2 |
| Curative | DICY | 4 | 4 | 4 | 4 | 4 |
| | FENURON | 0.15 | 0.15 | 0.15 | 0.15 | 0.15 |

Sample No. 100 is a control and was used for comparative purposes.

Each of Sample Nos. 100-104 were then cured for a period of time of 30 minutes at a temperature of 180° C. and evaluated for tensile shear strength and peel strength, the results of which are reported below in Table 16.

TABLE 16

| Sample No. | Physical Property | |
|---|---|---|
| | Tensile Shear Strength (N/mm²) | Tensile Peel Strength (N/mm) |
| 100 | 22.52 | 1.681 |
| 101 | 36.43 | 3.42 |
| 102 | 32.52 | 8.257 |
| 103 | 23.09 | 9.282 |
| 104 | 13.33 | 7.93 |

Sample No. 100 shows poor T-peel strength, whereas progressively increasing the level of Adduct AE in the compositions, such as to a level of 20-30 weight percent in Sample Nos. 102-103, increases both the tensile shear and T-peel strength, illustrating the usefulness of this adduct for toughening purposes.

Adduct AE was also used to formulate epoxy compositions with, and for comparison with, other toughening agents, as shown below in Table 17.

TABLE 17

| Composite | | Sample No. Amt. (wt. %) | | | | |
|---|---|---|---|---|---|---|
| Type | Identity | 105 | 106 | 107 | 108 | 109 |
| Epoxy | EPON 828 | 10 | 10 | 30 | 30 | 30 |
| Toughener | Adduct AE | — | 30 | 30 | 30 | 30 |
| | KANEKA MX 120* | 50 | 50 | — | — | — |
| | POLYDIS 3614 | — | — | — | 30 | — |
| | Epoxy-JEFFAMINE Adduct** | 30 | — | 30 | — | — |
| | Dow Adduct*** | — | — | — | — | 30 |
| Reactive Diluent | CARDOLITE 2513 | 4 | 4 | 4 | 4 | 4 |
| Silica Filler | AEROSIL R202 | 2 | 2 | 2 | 2 | 2 |
| Curative | DICY | 4 | 4 | 4 | 4 | 4 |
| | FENURON | 0.15 | 0.15 | 0.15 | 0.15 | 0.15 |

*masterbatch of 25 weight % nano-sized core-shell rubber in a matrix of bisphenol A diglycidyl ether epoxy resin, available commercially from Kaneka Corporation
**Prepared in accordance with U.S. Pat. No. 5,084,532 (Schenkel)
***Prepared in accordance with Examples 16-20 of U.S. Pat. No. 5,278,257 (Mulhaupt)

Sample No. 105 is a control and was used for comparative purposes.

Each of Sample Nos. 105-109 was evaluated for tensile shear strength and peel strength, the results of which are reported below in Table 18.

TABLE 18

| Sample No. | Physical Property | |
|---|---|---|
| | Tensile Shear (N/mm²) | Tensile Peel (N/mm) |
| 105 | 38.4 | 12.154 |
| 106 | 21.3 | 10.889 |
| 107 | 16.5 | 11.498 |
| 108 | 15.2 | 9.851 |
| 109 | 6.2 | 8.003 |

The results in Table 18 demonstrate the utility of Adduct AE as a co-toughener with the listed and evaluated tougheners. More specifically, when used in conjunction with either KANEKA MX 120 core shell rubber or the epoxy-JEFFAMINE adduct excellent T-peel strength values are attained compared to the control, although the tensile shear values appear to be negatively impacted.

Example 8

Blends of JEFFAMINE D2000 and 10%, 20% and 50% molar equivalents of DMS A12 (aminopropyl terminated PDMS, mol. wt. 800-1100) were each reacted with an appropriate amount of CBC to afford a resinous product consisting of a mixture of CBC blocked JEFFAMINE D2000 with 10%, 20% and 50% of CBC blocked PDMS as follows:

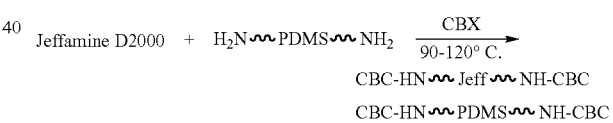

The resulting adduct is referred to as Adduct AD.

Tables 19A and 19B provide formulation information of samples prepared with CBC blocked JEFFAMINE and Adduct AD.

TABLE 19A

| Constituent | | Sample Nos./Amt. (wt %) | | | | | | |
|---|---|---|---|---|---|---|---|---|
| Type | Identity | 110 | 111 | 112 | 113 | 114 | 115 | 116 |
| Epoxy | EPON 828 | 60 | 80 | 70 | 60 | 50 | 80 | 70 |
| Toughener | CBC Blocked JEFFAMINE | 30 | — | — | — | — | — | — |
| | Adduct AD-1 | — | 10 | 20 | 30 | 40 | — | — |
| | Adduct AD-2 | — | — | — | — | — | 10 | 20 |
| | Adduct AD-3 | — | — | — | — | — | — | — |
| Reactive Diluent | CARDOLITE 2513 | 4 | 4 | 4 | 4 | 4 | 4 | 4 |
| Silica Filler | AEROSIL R202 | 2 | 2 | 2 | 2 | 2 | 2 | 2 |
| Curative | DICY | 4 | 4 | 4 | 4 | 4 | 4 | 4 |
| | FENURON | 0.15 | 0.15 | 0.15 | 0.15 | 0.15 | 0.15 | 0.15 |

TABLE 19B

| Constituent | | Sample Nos./Amt. (wt %) | | | | | |
|---|---|---|---|---|---|---|---|
| Type | Identity | 117 | 118 | 119 | 120 | 121 | 122 |
| Epoxy | EPON 828 | 60 | 50 | 80 | 70 | 60 | 50 |
| Toughener | CBC Blocked JEFFAMINE | | | | | | |
| | Adduct AD-1 | — | — | — | — | — | — |
| | Adduct AD-2 | 30 | 40 | — | — | — | — |
| | Adduct AD-3 | — | — | 10 | 20 | 30 | 40 |
| Reactive Diluent | CARDOLITE 2513 | 4 | 4 | 4 | 4 | 4 | 4 |
| Silica Filler | AEROSIL R202 | 2 | 2 | 2 | 2 | 2 | 2 |
| Curative | DICY | 4 | 4 | 4 | 4 | 4 | 4 |
| | FENURON | 0.15 | 0.15 | 0.15 | 0.15 | 0.15 | 0.15 |

Sample No. 110 is a control and is used for comparative purposes. Table 20 below provides T peel and tensile shear strength performance with Adducts AD-1, 2 and 3 in epoxy formulations, demonstrating the ability of those adducts to toughen such formulations.

TABLE 20

| Physical Property | Sample Nos. | | | | | | | | | | | | |
|---|---|---|---|---|---|---|---|---|---|---|---|---|---|
| | 110 | 111 | 112 | 113 | 114 | 115 | 116 | 117 | 118 | 119 | 120 | 121 | 122 |
| T-Peel (N/mm) | 8.12 | 0.7 | 8.2 | 9.6 | 9.7 | 1.0 | 1.9 | 6.1 | 8.5 | 2.1 | 5.9 | 6.0 | 3.5 |
| Tensile Shear (N/mm²) GBMS 30 mins. @ 180° C. | — | 6 | 2 | 8 | 0 | 1 | 4 | 0 | 6 | 1 | 3 | 1 | 6 |

The T peel and tensile shear strength evaluations were performed in accordance with the following respective parameters:

| 180° Tensile Peel ASTM D1876 | |
|---|---|
| Specimens: | Grit Blasted Mild Steel (GBMS), 1.00 mm substrate thickness |
| Bondline: | 0.25 mm |
| Testing rate: | 200 mm/min |
| Test temperature: | Ambient, 0, −10, −20, −30, −40° C. |

| Tensile Lap Shear ASTM D1002 | |
|---|---|
| Specimens: | Grit Blasted Mild Steel (GBMS), 1.6 mm substrate thickness |
| Bondline: | 0.05 mm |
| Testing rate: | 200 mm/min |
| Test temperature: | Ambient |

Use of this adduct provides a means of incorporating a PDMS into the cured epoxy network via the masked isocyanate functionality which is unblocked during cure.

What is claimed is:

1. An adduct as set forth below:

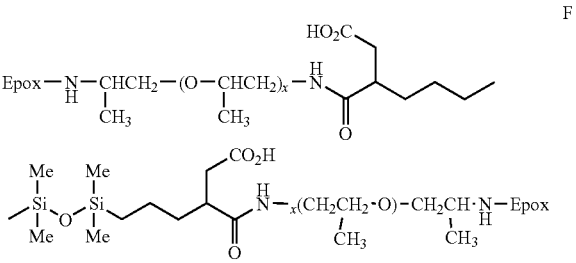

F

2. A curable composition comprising:
   a. a thermosetting component; and
   b. an adduct according to claim 1.

3. The composition of claim 2, wherein the thermosetting component is a member selected from the group consisting of epoxies, episuifides, benzozaxines and combinations thereof.

4. The composition of claim 2, wherein the thermosetting component is a member selected from the group consisting of

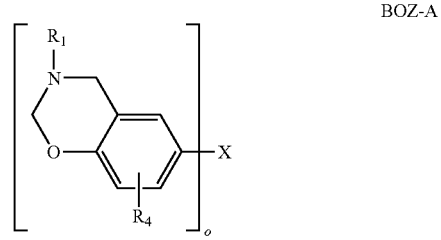

BOZ-A wherein o is 1-4, X is selected from a direct bond (when o is 2), alkyl (when o is 1), alkylene (when o is 2-4), carbonyl (when o is 2), thiol (when o is 1), thioether (when o is 2), sulfoxide (when o is 2), and sulfone (when o is 2), R1 is selected from hydrogen, alkyl, alkenyl and aryl, and $R_4$ is selected from hydrogen, halogen, alkyl and alkenyl;

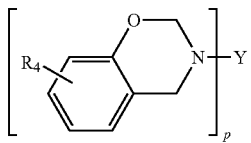

BOZ-B wherein p is 2, Y is selected from biphenyl (when p is 2), diphenyl methane (when p is 2), diphenyl isopropane (when p is 2), diphenyl sulfide (when p is 2), diphenyl sulfoxide(when p is 2), diphenyl sulfone (when p is 2), and diphenyl ketone (when p is 2), and $R_4$ is selected from hydrogen, halogen, alkyl and alkenyl.

5. A curable composition comprising claim 2, further comprising a toughner.

6. An adduct as set forth below:

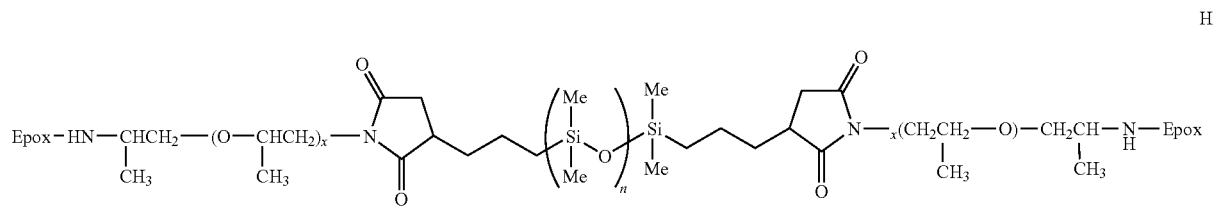

H

7. A curable composition comprising:
   a. a thermosetting component; and
   b. an adduct according to claim 6.

8. The composition of claim 7, wherein the thermosetting component is a member selected from the group consisting of epoxies, episulfides, benzozaxines and combinations thereof.

9. A curable composition comprising claim 7, further comprising a toughner.

10. An adduct as set forth below:

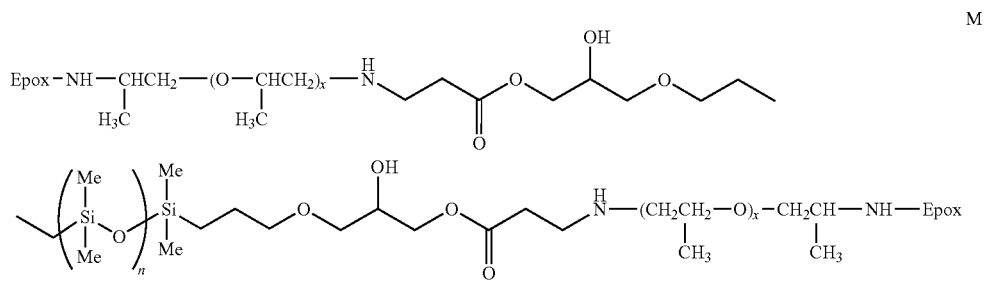

M

11. A curable composition comprising:
    a. a thermosetting component; and
    b. an adduct according to claim 10.

12. The composition of claim 11, wherein the thermosetting component is a member selected from the group consisting of epoxies, episulfides, benzozaxines and combinations thereof.

13. A curable composition comprising claim 11, further comprising a toughener.

14. An adduct as set forth below:

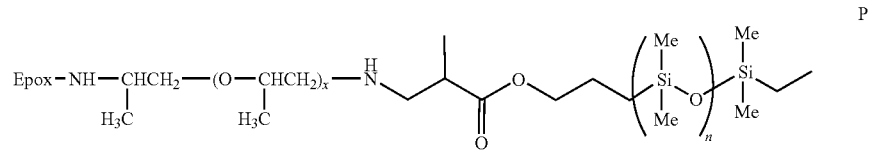

P

-continued
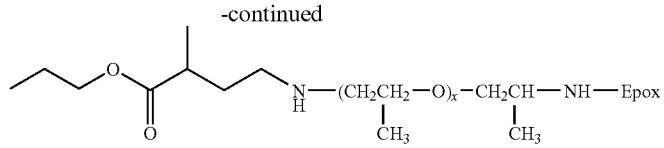
15. A curable composition comprising:
a. a thermosetting component;
b. an adduct according to claim 14.
16. The composition of claim 15, wherein the thermosetting component is a member selected from the group consisting of epoxies, episulfides, benzozaxines and combinations thereof.
17. A curable composition comprising claim 15, further comprising a toughener.
* * * * *